(12) United States Patent
Logsdon et al.

(10) Patent No.: US 10,428,159 B2
(45) Date of Patent: Oct. 1, 2019

(54) BLOCKING MONOCLONAL ANTIBODIES TO AGR2 AND ITS RECEPTOR C4.4A

(71) Applicant: Board of Regents, The University of Texas System, Austin, TX (US)

(72) Inventors: Craig D. Logsdon, Houston, TX (US); Vijaya Ramachandran, Pearland, TX (US); Thiruvengadam Arumugam, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/509,790

(22) PCT Filed: Sep. 8, 2015

(86) PCT No.: PCT/US2015/048936
§ 371 (c)(1),
(2) Date: Mar. 8, 2017

(87) PCT Pub. No.: WO2016/040321
PCT Pub. Date: Mar. 17, 2016

(65) Prior Publication Data
US 2017/0283509 A1  Oct. 5, 2017

Related U.S. Application Data

(60) Provisional application No. 62/048,037, filed on Sep. 9, 2014.

(51) Int. Cl.
| | | |
|---|---|---|
| *A61K 39/395* | (2006.01) | |
| *C07K 16/28* | (2006.01) | |
| *C07K 16/30* | (2006.01) | |
| *C07K 16/40* | (2006.01) | |
| *A61K 45/06* | (2006.01) | |
| *C12N 15/113* | (2010.01) | |
| *A61K 39/00* | (2006.01) | |

(52) U.S. Cl.
CPC .......... *C07K 16/40* (2013.01); *A61K 39/3955* (2013.01); *A61K 39/39558* (2013.01); *A61K 45/06* (2013.01); *C07K 16/28* (2013.01); *C07K 16/30* (2013.01); *C07K 16/303* (2013.01); *C12N 15/1138* (2013.01); *A61K 2039/505* (2013.01); *A61K 2039/507* (2013.01); *C07K 2317/21* (2013.01); *C07K 2317/24* (2013.01); *C07K 2317/34* (2013.01); *C07K 2317/35* (2013.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/622* (2013.01); *C07K 2317/73* (2013.01); *C07K 2317/76* (2013.01); *C12N 2310/14* (2013.01)

(58) Field of Classification Search
CPC ...... A61K 39/395; C07K 16/28; C07K 16/30; C07K 16/40
See application file for complete search history.

(56) References Cited

U.S. PATENT DOCUMENTS

| 9,574,012 B2* | 2/2017 | Li | C07K 16/40 |
|---|---|---|---|
| 2005/0147612 A1* | 7/2005 | Yayon | C07K 16/2863 |
| | | | 424/146.1 |
| 2012/0321619 A1 | 12/2012 | Linden | |
| 2014/0328829 A1 | 11/2014 | Li | |
| 2015/0376276 A1* | 12/2015 | Lewis | C07K 16/2803 |
| | | | 424/133.1 |

FOREIGN PATENT DOCUMENTS

| EP | 2749573 | 7/2014 |
|---|---|---|
| WO | 2016040321 | 3/2016 |
| WO | 2017156280 | 9/2017 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Padlan, Advances in Protein Chemistry, 1996, 49:57-133.*
Berglund et al., Protein Science, 2008, 17:606-613.*
Tzartos et al., Methods in Molecular Biology, 1996, 66:55-66.*
International Search Report and Written Opinion for PCT Application No. PCT/US2017/021587, dated May 26, 2017, filed on Mar. 9, 2017, 9 pages.
Miyake T et al., C4.4A highly expressed in HER2-positive human breast cancers may indicate a good prognosis, Breast Cancer. Jul. 2015;22(4):366-373.
Hrstka R, etal., The pro-metastatic protein anterior gradient-2 predicts poor prognosis in tamoxifen-treated breast cancers, Oncogene. Aug. 26, 2010;29(34):4838-4847.
Wang Y et al., Different Mechanisms for resistance to trastuzumab versus lapatinib in HER2—positive breat cancers—role of estrogen receptor and HER2 reactivation, Breast Cancer Research, 28, Nov. 2011, vol. 13, Iss. 6, pp. 1-19, entire document.
International Search Report (ISR) and Written Opinion of the International Searching Authority (WO of the ISA) , dated May 26, 2017, International Application No. PCT/US2017/021587 (WO2016040321), 12 pgs.

(Continued)

*Primary Examiner* — Hong Sang
(74) *Attorney, Agent, or Firm* — Dennis A. Bennett; Charles H. Rexer, Jr.

(57) ABSTRACT

Provided herein are monoclonal antibodies that recognize, bind to, and block interactions of other molecules with AGR2 and C4.4A. Also provided herein are methods of using anti-AGR2 and anti-C4.4A antibodies to treat cancer.

17 Claims, 35 Drawing Sheets
Specification includes a Sequence Listing.

(56) References Cited

OTHER PUBLICATIONS

Gray TA et al., Anterior Gradient-3: a novel biomarker for ovarian cancer that mediates cisplatin resistance in xenograft models, Journal of Immunological Methods, Apr. 30, 2012;378(1-2):pp. 20-32.
Fletcher GC et al., hAG-2 and hAG-3, human homologues of genes involved in differentiation, are associated with oestrogen receptor-positive breast tumours and interact with metastasis gene C4.4a and dystroglycan, British Journal of Cancer. Feb. 24, 2003;88(4):pp. 579-585.
Arumugam T et al., New Blocking Antibodies against Novel AGR2-C4.4A Pathway Reduce Growth and Metastasis of Pancreatic Tumors and Increase Survival in Mice, Molecular Cancer Therapeutics. Apr. 2015;14(4):pp. 941-951.

* cited by examiner

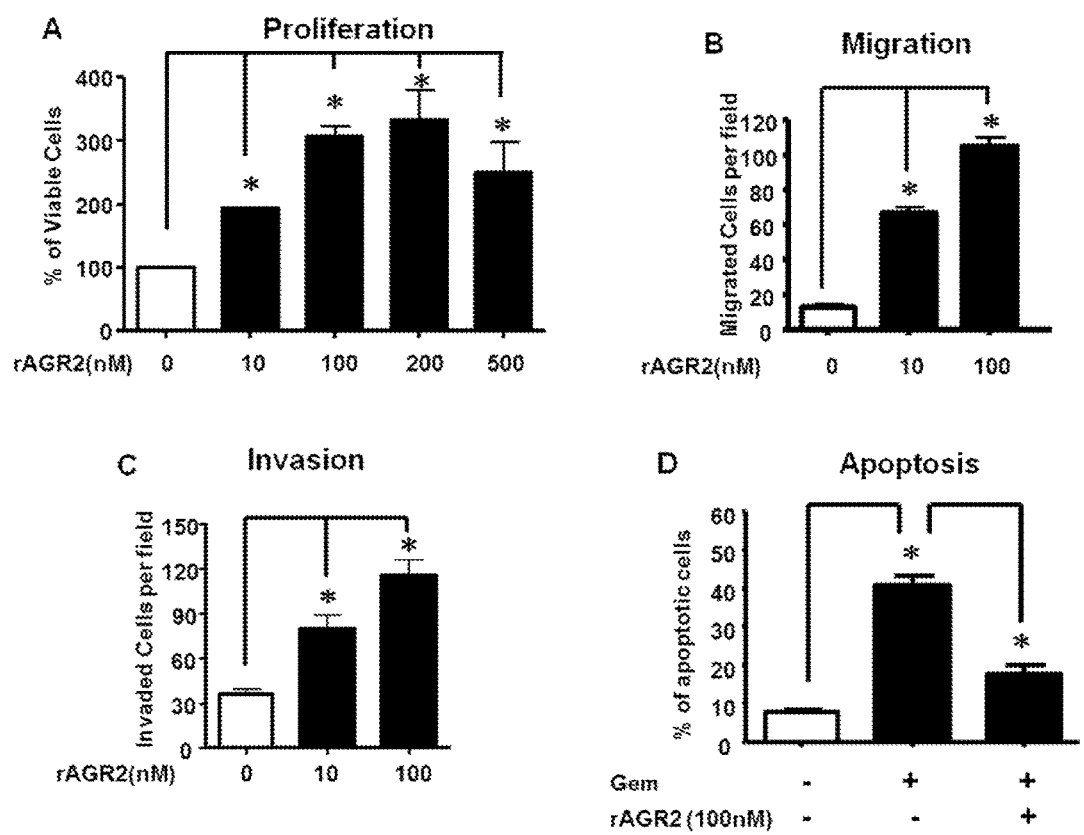
FIGs. 1A-D

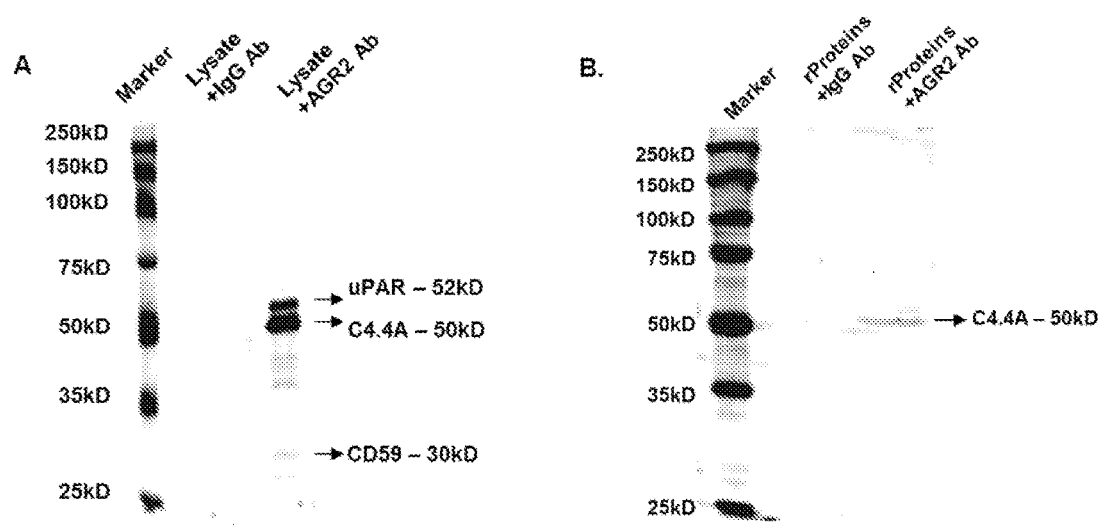
FIGs. 2A-B

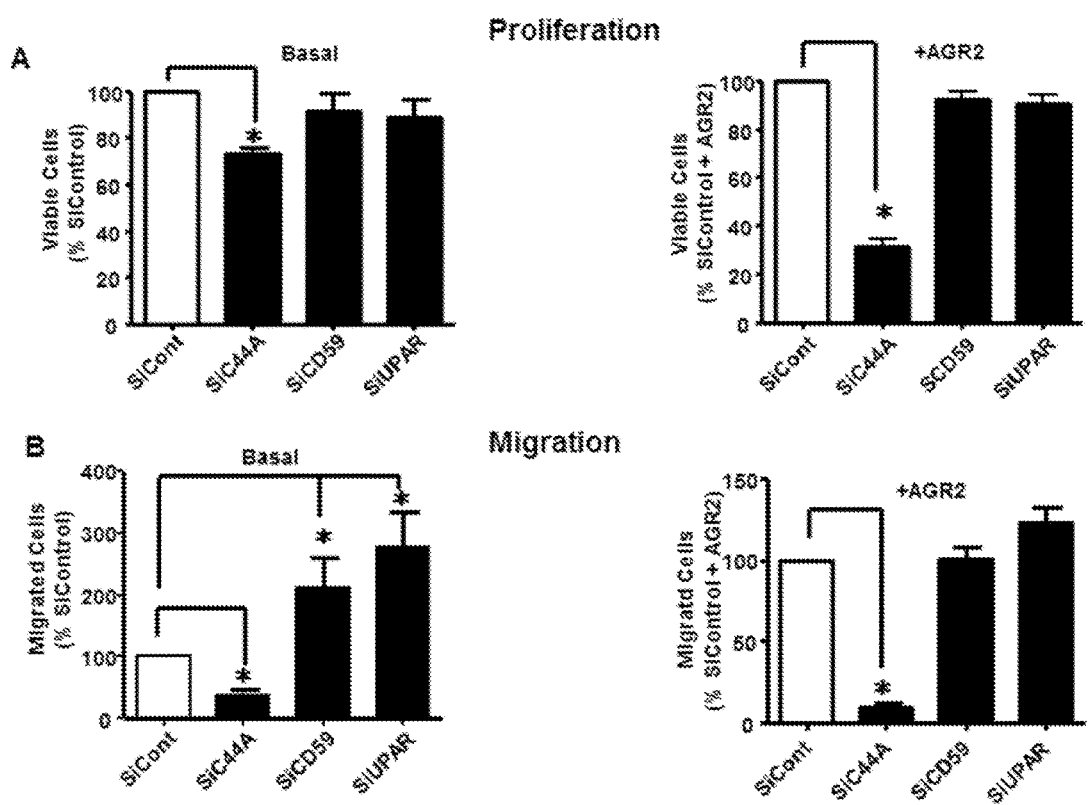
FIGs. 3A-B

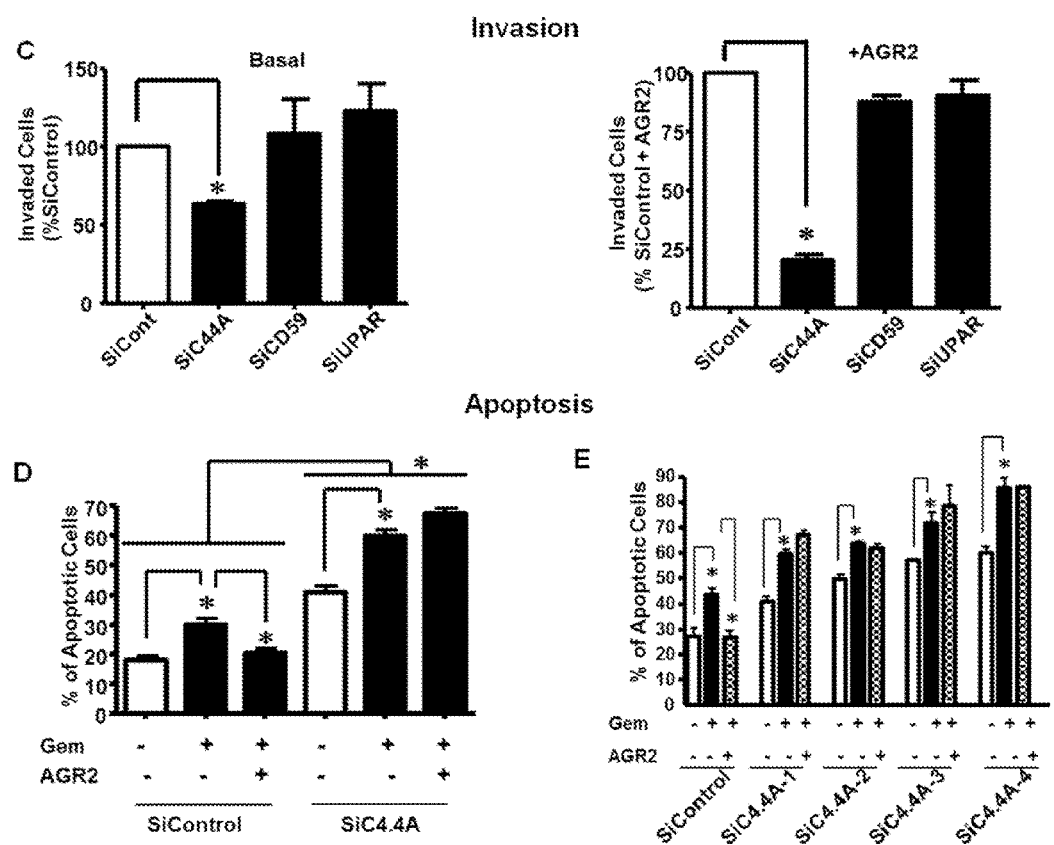
FIGs. 3C-E

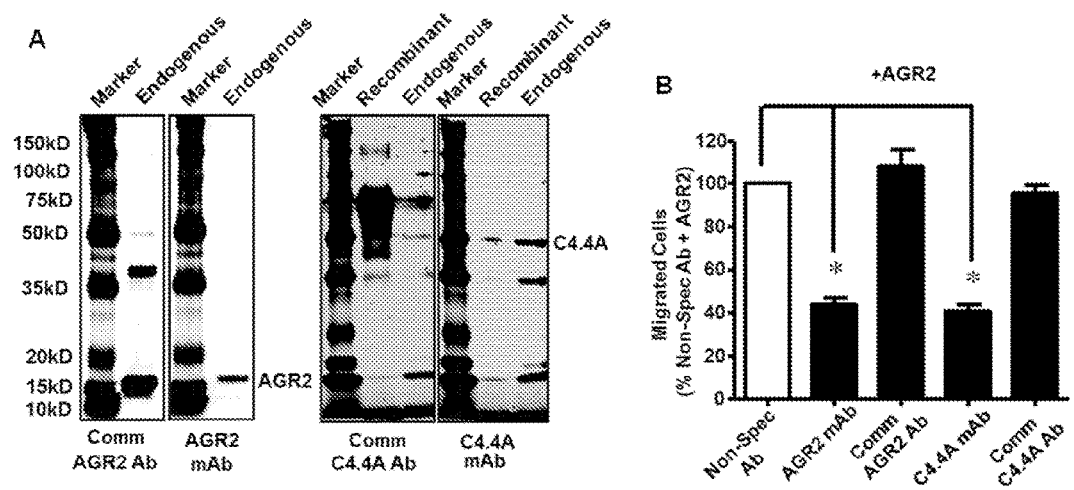
FIGs. 5A-B

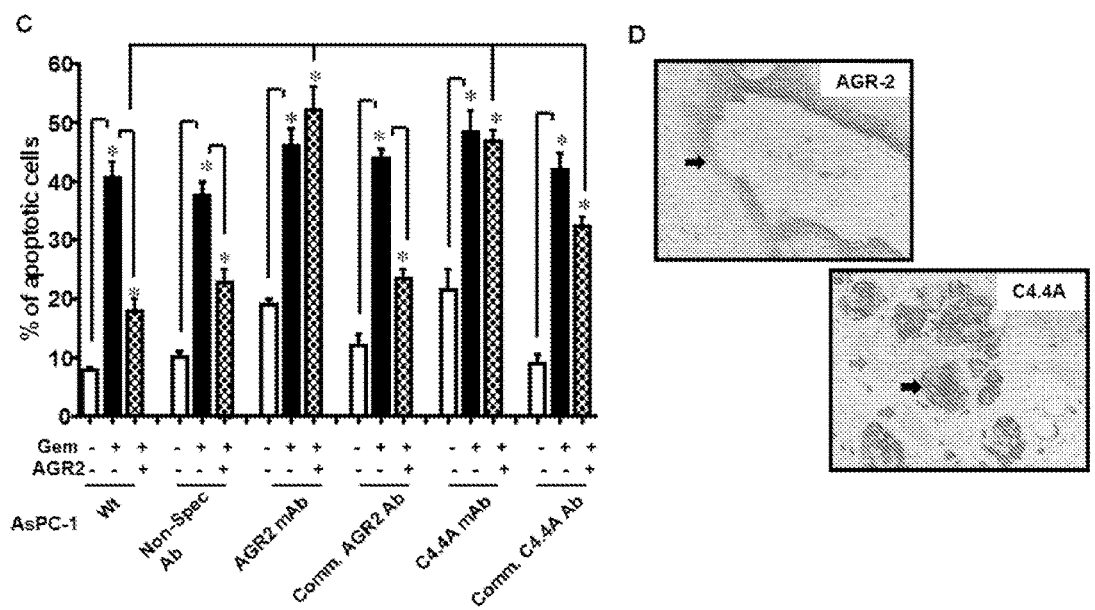
FIGs. 5C-D

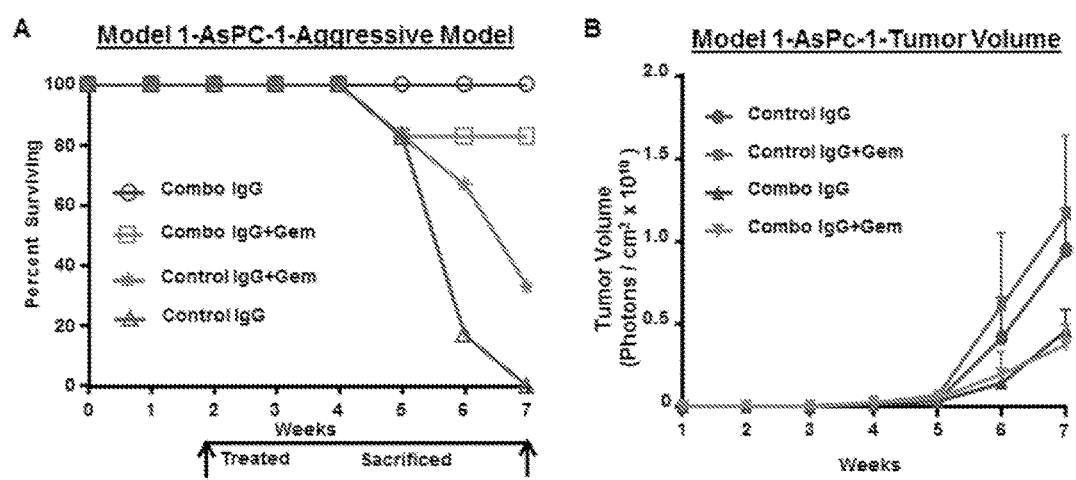
FIGs. 6A-B

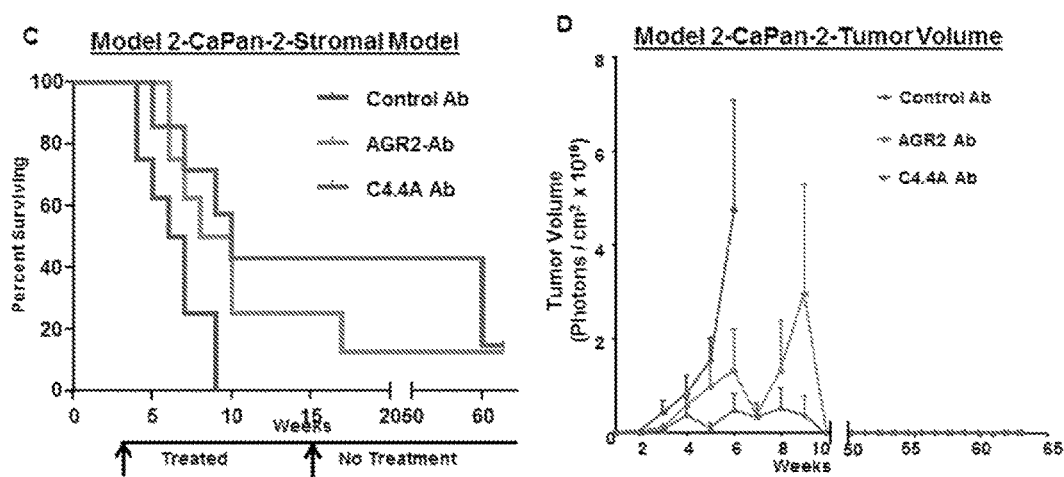
FIGs. 6C-D

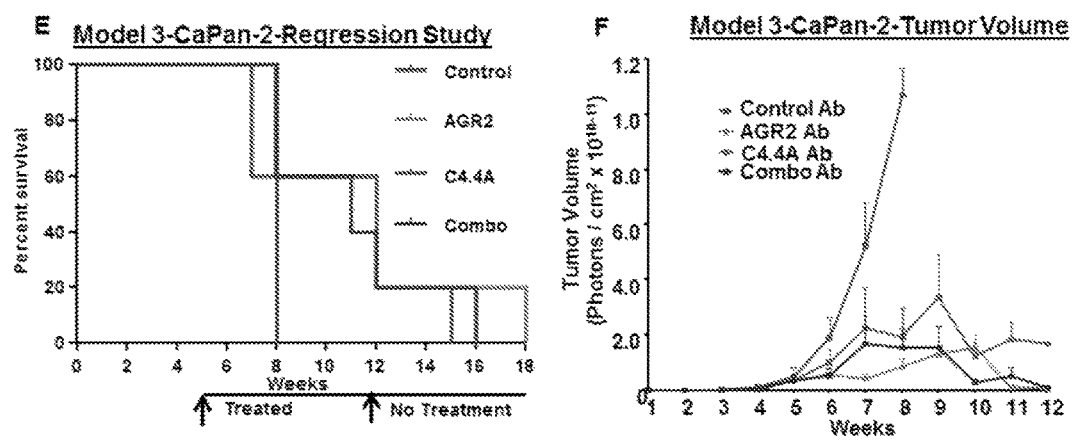
FIGs. 6E-F

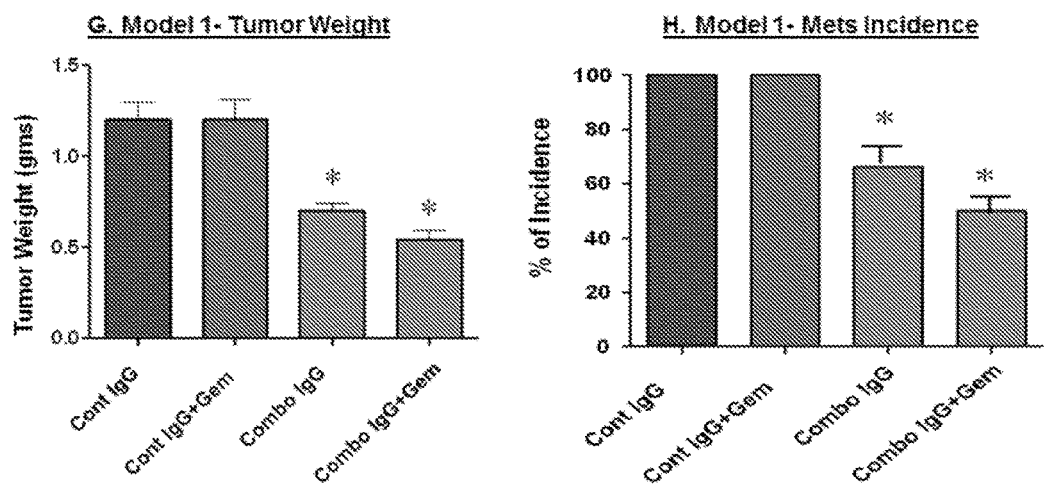
FIGs. 6G-H

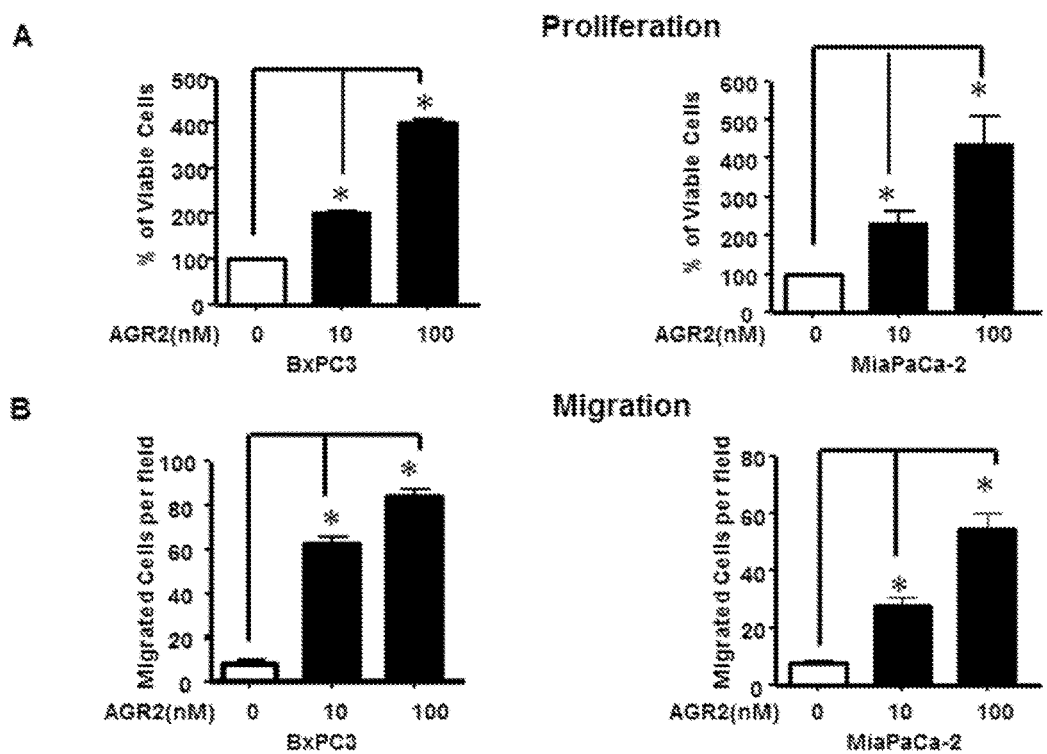
FIGs. 7A-B

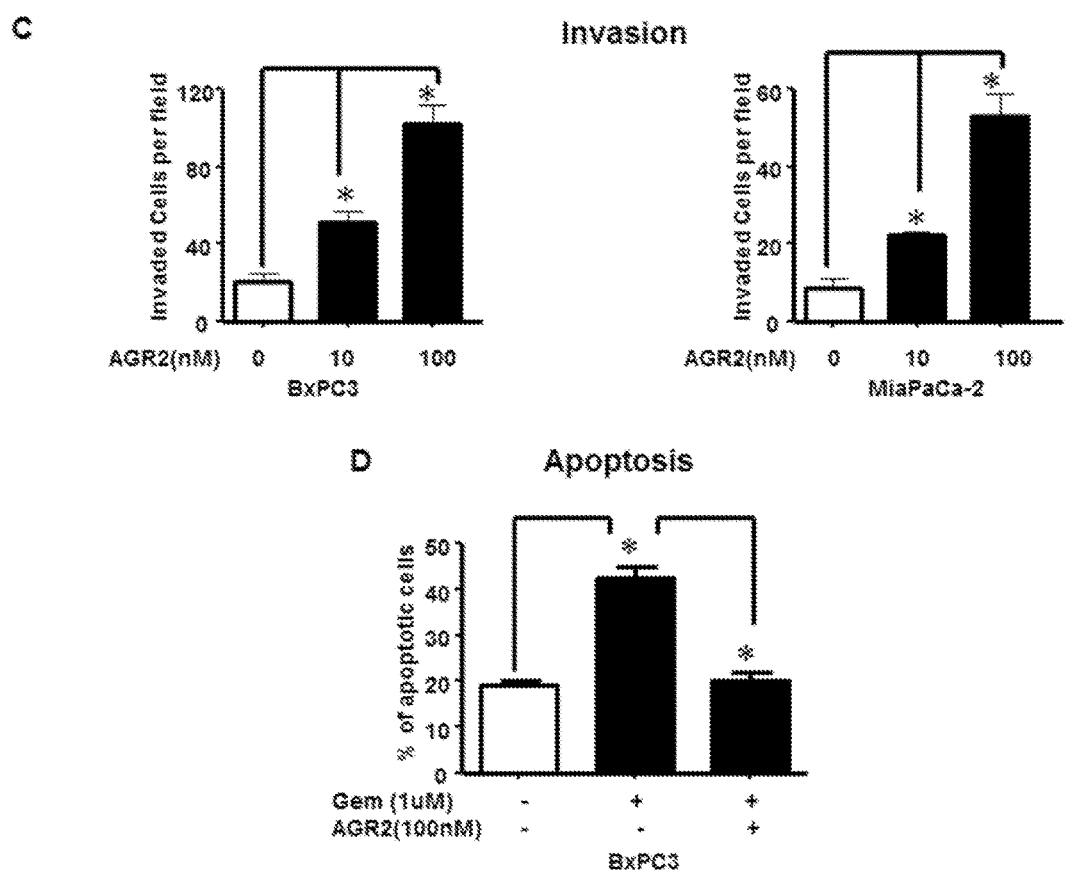
FIGs. 7C-D

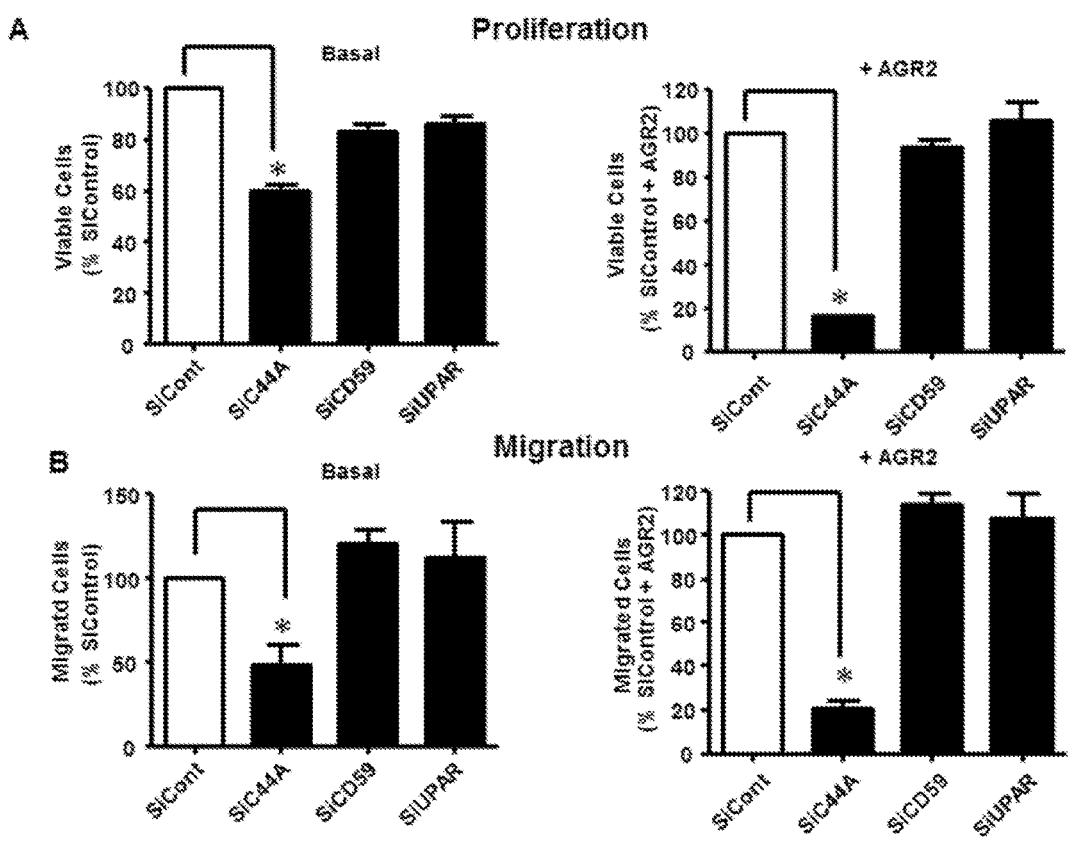
FIGs. 9A-B

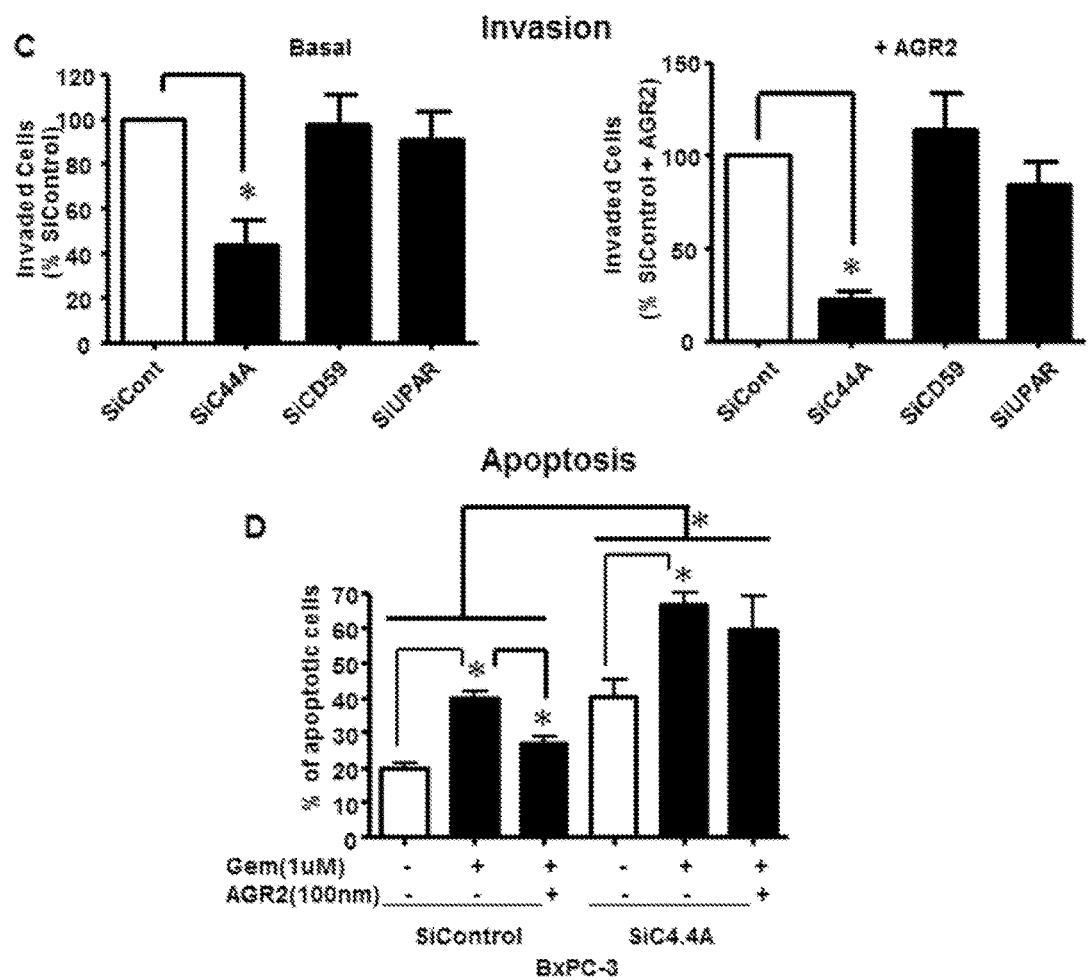
FIGs. 9C-D

BLOCKING MONOCLONAL ANTIBODIES TO AGR2 AND ITS RECEPTOR C4.4A

This application is a U.S. national stage filing under 35 U.S.C. § 371 of PCT International Application No. PCT/US2015/048936, filed Sep. 8, 2015, which in turn claims the benefit of priority of U.S. Provisional Application No. 62/048,037, filed Sep. 9, 2014, the disclosures of which are hereby incorporated by reference as if written herein in their entireties.

BACKGROUND OF THE INVENTION

1. Field of the Invention

The present invention relates generally to the fields of cellular biology and oncology. More particularly, it concerns AGR2 and C4.4A-binding antibodies and methods of their use in anti-cancer therapies.

2. Description of Related Art

Anterior Gradient 2 (AGR2 [also called hAG-2 (Thompson and Weigel, 1998) or Gob-4 (Komiya et al., 1999)]) is the human orthologue of the *Xenopus laevis*, XAG-2. XAG-2 is secreted and takes part in ectodermal patterning of the frog embryo and in amphibian limb regeneration by interacting with the receptor Prod-1 of the Ly6 superfamily (Aberger et al., 1998; Kumar et al., 2007; da Silva et al., 2002). However, there is no human homologue of Prod-1. It is unknown whether AGR2 functions through a receptor on the cell surface or functions within cells in humans. The tissue distribution of AGR2 in healthy adult humans indicates that it is restricted to organs possessing mucin producing cells. A mouse genetic deletion model of AGR2 showed alterations in mucin synthesis (Park et al., 2009). Other studies have supported the concept that AGR2 possesses sequence similarity to the protein disulfide isomerase (PDI) family (Zhao et al., 2010; Altschul et al., 1997; Persson et al., 2005; Gupta et al., 2012). A member of the PDI protein family may catalyze formation, reduction and isomerization of disulfide bonds, thereby stabilizing intermediate conformations during protein maturation in the ER (Persson et al., 2005). However, a role of AGR2 in protein synthesis in normal cells does not resemble its actions in amphibians and also does not explain its observed roles in cancer.

AGR2 has been reported to bind to dystroglycan-1 (DAG-1) and C4.4A based on yeast two-hybrid results (Fletcher et al., 2003). However, no evidence was provided to support the interactions of these molecules in mammalian cells or to demonstrate the biological function of these interactions. AGR2 is expressed in a wide variety of tumors formed in different tissues with diverse patterns of genetic alterations including pancreatic ductal adenocarcinoma (PDAC) (Ramachandran et al., 2008) and cancers of the breast (Thompson and Weigel, 1998; Fletcher et al., 2003), prostate (Zhang et al., 2005), lung (Zhu et al., 2007), and colorectum (Smirnov et al., 2005). AGR2 supports aggressive growth and metastasis of a variety of cancer cells (Liu et al., 2005; Innes et al., 2006; Barraclough et al., 2009). Hence, AGR2 and its receptor may serve as useful therapeutic targets.

SUMMARY OF THE INVENTION

Herein, C4.4A (LYPD3) was identified as the functional cell surface receptor for extracellular AGR2. Novel monoclonal blocking antibodies against both AGR2 and C4.4A are provided herein as well as methods of their use in treating cancer.

In some embodiments, the present invention is directed towards an isolated or recombinant monoclonal antibody or antigen binding fragment thereof that specifically binds to an AGR2 polypeptide. In certain aspects, an antibody specifically binds to an AGR2 polypeptide corresponding to amino acids 25-125 of SEQ ID NO: 26. In certain aspects, an antibody specifically binds to an AGR2 polypeptide according to SEQ ID NO: 28. SEQ ID NO: 28 corresponds to amino acid residues the 75 to 103 of human AGR2 (SEQ ID NO: 26). The inventors have found that a monoclonal antibody, or antigen binding fragment thereof, having the specificity for the AGR2 polypeptide as defined above, provides notable advantages in use compared to the prior art antibodies against AGR2, notably the monoclonal antibody, Ab56703. In a further aspect, a monoclonal antibody, or antigen binding fragment thereof, having the specificity for the AGR2 polypeptide as defined above, inhibits tumor cell pancreatic ductal adenocarcinoma migration and resistance to gemcitabine-induced apoptosis. In certain aspects, an antibody competes for the binding of an AGR2 polypeptide with the 163-28B-1 monoclonal antibody. In certain aspects, the antibody may comprise all or part of the heavy chain variable region and/or the light chain variable region of the 163-28B-1 monoclonal antibody. In a further aspect, the antibody may comprise an amino acid sequence that corresponds to a first, second, and/or third complementarity determining region (CDR) from the light variable and/or heavy variable chain of the 163-28B-1 monoclonal antibody of the present embodiment.

In certain aspects, the isolated antibody comprises CDR sequences at least 80%, 90% or 95% identical to the CDR regions of the 163-28B-1 heavy and light chain amino acid sequences. In further aspects, an antibody comprises CDR regions identical to 163-28B-1, except for one or two amino acid substitutions, deletions or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of the 163-28B-1 monoclonal antibody. Thus, in some specific aspects, an antibody of the embodiments comprises (a) a first VH CDR at least 80% identical to VH CDR1 of 163-28B-1 (SEQ ID NO: 20); (b) a second VH CDR at least 80% identical to VH CDR2 of 163-28B-1 (SEQ ID NO: 21); (c) a third VH CDR at least 80% identical to VH CDR3 of 163-28B-1 (SEQ ID NO: 22); (d) a first VL CDR at least 80% identical to VL CDR1 of 163-28B-1 (SEQ ID NO: 23); (e) a second VL CDR at least 80% identical to VL CDR2 of 163-28B-1 (SEQ ID NO: 24); and (f) a third VL CDR at least 80% identical to VL CDR3 of 163-28B-1 (SEQ ID NO: 25).

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody 163-28B-1, which are represented by SEQ ID NOs: 20, 21, 22, 23, 24 and 25, respectively. In one aspect, the isolated antibody comprises CDR sequences that are identical to the CDR sequences of monoclonal antibody 163-28B-1.

In another aspect, the isolated antibody comprises a $V_H$ domain at least about 80% identical to the $V_H$ domain of 163-28B-1 (SEQ ID NO: 18) and a $V_L$ domain at least about 80% identical to the $V_L$ domain of 163-28B-1 (SEQ ID NO: 19). In one aspect, the isolated antibody comprises $V_H$ and $V_L$ domains identical to those of monoclonal antibody 163-28B-1. In a further aspect, the isolated antibody is the 163-28B-1 antibody.

In some embodiments, the present invention is directed towards an isolated or recombinant monoclonal antibody or antigen binding fragment thereof that specifically binds to a C4.4A polypeptide. In certain aspects, an antibody specifically binds to a C4.4A polypeptide corresponding to amino acids 240-340 of SEQ ID NO: 27. In certain aspects, an antibody specifically binds to a C4.4A epitope within the C4.4A polypeptide according to SEQ ID NO: 29. SEQ ID NO: 29 corresponds to amino acid residues the 262 to 296 of human C4.4A (SEQ ID NO:27). The inventors have found that a monoclonal antibody, or antigen binding fragment thereof, having the specificity defined above, provides notable advantages in use compared to the prior art antibodies against C4.4A, notably the polyclonal antibody, AF5428. In a further aspect, a monoclonal antibody, or antigen binding fragment thereof, having the specificity for the C4.4A polypeptide defined above, inhibits tumor cell pancreatic ductal adenocarcinoma migration and resistance to gemcitabine-induced apoptosis. In certain aspects, an antibody competes for the binding of a C4.4A polypeptide with the 162-1A-1 monoclonal antibody. In certain aspects, the antibody may comprise all or part of the heavy chain variable region and/or the light chain variable region of the 162-1A-1 monoclonal antibody. In a further aspect, the antibody may comprise an amino acid sequence that corresponds to a first, second, and/or third complementarity determining region (CDR) from the light variable and/or heavy variable chain of the 162-1A-1 monoclonal antibody of the present embodiment.

In certain aspects, the isolated antibody comprises CDR sequences at least 80%, 90% or 95% identical to the CDR regions of the 162-1A-1 heavy and light chain amino acid sequences. In further aspects, an antibody comprises CDR regions identical to 162-1A-1, except for one or two amino acid substitutions, deletions or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of the 162-1A-1 monoclonal antibody. Thus, in some specific aspects, an antibody of the embodiments comprises (a) a first VH CDR at least 80% identical to VH CDR1 of 162-1A-1 (SEQ ID NO: 12); (b) a second VH CDR at least 80% identical to VH CDR2 of 162-1A-1 (SEQ ID NO: 13); (c) a third VH CDR at least 80% identical to VH CDR3 of 162-1A-1 (SEQ ID NO: 14); (d) a first VL CDR at least 80% identical to VL CDR1 of 162-1A-1 (SEQ ID NO: 15); (e) a second VL CDR at least 80% identical to VL CDR2 of 162-1A-1 (SEQ ID NO: 16); and (f) a third VL CDR at least 80% identical to VL CDR3 of 162-1A-1 (SEQ ID NO: 17).

In further aspects, the isolated antibody comprises a first $V_H$, a second $V_H$, a third $V_H$, a first $V_L$, a second $V_L$, and a third $V_L$ CDR sequence at least 80% identical to the corresponding CDR sequence of monoclonal antibody 162-1A-1, which are represented by SEQ ID NOs: 12, 13, 14, 15, 16, and 17, respectively. In one aspect, the isolated antibody comprises CDR sequences that are identical to the CDR sequences of monoclonal antibody 162-1A-1.

In another aspect, the isolated antibody comprises a $V_H$ domain at least about 80% identical to the $V_H$ domain of 162-1A-1 (SEQ ID NO: 10) and a $V_L$ domain at least about 80% identical to the $V_L$ domain of 162-1A-1 (SEQ ID NO: 11). In one aspect, the isolated antibody comprises $V_H$ and $V_L$ domains identical to those of monoclonal antibody 162-1A-1. In a further aspect, the isolated antibody is the 162-1A-1 antibody.

In some aspects, an antibody of the embodiments may be an IgG (e.g., IgG1, IgG2, IgG3 or IgG4), IgM, IgA, or an antigen binding fragment thereof. The antibody may be a Fab', a F(ab')2 a F(ab')3, a monovalent scFv, a bivalent scFv, or a single domain antibody. The antibody may be a human, humanized, or de-immunized antibody. In some aspects, the antibody may be conjugated to an imaging agent, a chemotherapeutic agent, a toxin, or a radionuclide.

In one embodiment, there is provided a recombinant polypeptide comprising an antibody $V_H$ domain comprising CDRs 1-3 of the $V_H$ domain of 163-28B-1 (SEQ ID NOs: 20, 21, and 22) or CDRs 1-3 of the $V_H$ domain of 162-1A-1 (SEQ ID NOs: 12, 13, and 14). In another embodiment, there is provided a recombinant polypeptide comprising an antibody $V_L$ domain comprising CDRs 1-3 of the $V_L$ domain of 163-28B-1 (SEQ ID NOs: 23, 24, and 25) or 162-1A-1 (SEQ ID NOs: 15, 16, and 17).

In some embodiments, there is provided an isolated polynucleotide molecule comprising nucleic acid sequence encoding an antibody or a polypeptide comprising an antibody $V_H$ or $V_L$ domain disclosed herein.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present invention comprising expressing one or more polynucleotide molecule(s) encoding a $V_L$ or $V_H$ chain of an antibody disclosed herein in a cell and purifying the antibody from the cell.

In additional embodiments, there are pharmaceutical compositions comprising an antibody or antibody fragment as discussed herein. Such a composition further comprises a pharmaceutically acceptable carrier and may or may not contain additional active ingredients.

In embodiments of the present invention, there is provided a method for treating a subject having a cancer comprising administering to the subject an effective amount of an agent that inhibits the AGR2/C4.4A autocrine signaling loop. In one aspect, the agent may be an agent that disrupts the AGR2/C4.4A interaction.

In embodiments of the present invention, there is provided a method for treating a subject having a cancer comprising administering an effective amount of an antibody disclosed herein. In certain aspects, the antibody is a monoclonal antibody of the present invention, such as 162-1A-1 or 163-28B-1, or a recombinant polypeptide comprising antibody segment derived therefrom.

In certain aspects, the cancer may be a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In one aspect, the cancer may be a pancreatic ductal adenocarcinoma.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy. In one aspect, the subject may be a human subject.

In further aspects, the method may further comprise administering a composition of the present invention more than one time to the subject, such as, for example, 1, 2, 3, 4, 5, 6, 7, 8, 9, 10, 15, 20 or more times.

In accordance with certain aspects of the present invention, there is provided a method for treating cancer comprising administering an amount of an AGR2-binding protein and/or an C4.4A-binding protein effective to treat the cancer of the patient. In some aspects, a method comprises treating a patient who either has previously been determined to have a cancer or is determined to have a cancer, such as a pancreatic ductal adenocarcinoma.

In certain embodiments, the AGR2-binding protein and/or C4.4A-binding protein may be an antibody, which may be a monoclonal antibody, a polyclonal antibody, a chimeric antibody, an affinity matured antibody, a humanized antibody, a human antibody, or an antigen-binding antibody fragment. Preferably, the antibody is a monoclonal antibody or a humanized antibody. In embodiments where the antibody is an antibody fragment, preferred fragments include Fab, Fab', Fab'-SH, F(ab')$_2$, or scFv molecules.

For certain medical or clinical applications, the antibody may be attached to an agent to be targeted to a C4.4A-expressing cell. The agent may be a cytotoxic agent, a cytokine, an anti-angiogenic agent, a chemotherapeutic agent, a diagnostic agent, an imaging agent, a radioisotope, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a microparticle, a nanoparticle, a magnetic bead, a microdevice, a cell, a nucleic acid, or an expression vector. Where the targeted molecule is a protein, the coding regions for the respective protein molecule and antibody may be aligned in frame to permit the production of a "fused" molecule where desired. In other embodiments, however, the antibody may be conjugated to the molecule using conventional conjugation techniques.

Certain embodiments are directed to an antibody or recombinant polypeptide composition comprising an isolated and/or recombinant antibody or polypeptide that specifically binds AGR2 or C4.4A. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a AGR2-binding antibody or C4.4A-binding antibody as provided in Table 1.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a AGR2-binding antibody or a C4.4A-binding antibody as provided in Table 1.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a AGR2-binding antibody or C4.4A-binding antibody (as provided in Table 1). For example, a polypeptide may comprise 1, 2 or 3 amino acid segments that are at least 80, 85, 90, 95, 96, 97, 98, 99, or 100% identical (or any range derivable therein) to CDRs 1, 2, and/or 3 of a AGR2-binding antibody or C4.4A-binding antibody as provided in Table 1.

In one embodiment, a composition comprising an AGR2-binding antibody and/or C4.4A-binding antibody is provided for use in the treatment of cancer in a patient. In another embodiment, the use of a AGR2-binding antibody and/or C4.4A-binding antibody in the manufacture of a medicament for the treatment of a cancer is provided. Said AGR2-binding antibody and/or C4.4A-binding antibody may be any AGR2-binding antibody and/or C4.4A-binding antibody of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. Extracellular AGR2 stimulates PDAC cell aggressiveness. Extracellular addition of rAGR2 (0-500 nM) to AsPC-1 cells led to a dose-dependent increase in (A) cell proliferation, (B) migration, and (C) invasion. (D) Gemcitabine (Gem) addition resulted in increased apoptosis. Proliferation is shown as percent of viable cells over the control. However, extracellular AGR2 significantly reduced the level of Gem-induced apoptosis. Data shown are mean±SEM for 3 experiments ($*p<0.05$).

FIGS. 2A-C. C4.4A and other LY6 family receptors interact with AGR2. (A) Several candidate receptors (uPAR, C4.4A, and CD59) co-immunoprecipitated with AGR2, while DAG-1 did not. (B) Purified recombinant AGR2 and C4.4A were also co-immunoprecipitated from their suspension, supporting a direct interaction of AGR2 and C4.4A. (C) Silencing of C4.4A, CD59, and uPAR was accomplished using siRNAs at two different concentrations. Significant silencing was shown by western blotting with respective antibodies and the same membranes were blotted for β-actin, which served as a loading control. Both concentrations of siRNA showed significant silencing. Micrographs shown are representative of three independent experiments.

FIGS. 3A-E. C4.4A is required for rAGR2-mediated functions. AsPC-1 cells were transfected with siRNAs to silence C4.4A, CD59, or uPAR and then treated without (basal, left column) and with AGR2 (100 nM, right column) daily. Only C4.4A silencing reduced both basal and rAGR2-stimulated (A) proliferation, (B) migration, and (C) invasion. Proliferation is shown as percent of viable cells over the SiControl (basal) and SiControl+AGR2 (treated). (D) In SiControl cells, Gem addition stimulated apoptosis and this effect was ameliorated by AGR2. Silencing of C4.4A itself induced apoptosis, improved Gem-mediated apoptosis, and abolished the survival effects of AGR2 showing significant increase in apoptosis. Data shown are mean±SEM for 3 experiments ($*p<0.05$). (E) To determine the effects of specific C4.4A siRNAs, four siRNAs (SiC4.4A 1-4) were used for apoptosis studies and had comparable results.

FIGS. 5A-D. Monoclonal antibodies with high specificity were developed that block AGR2/C4.4A binding and biological effects. (A) From the endogenous PDAC cell lysate (SU86.86), AGR2 (18 kD) and C4.4A (50 kD) were identified by their respective newly developed mAbs. Extra bands identified with the endogenous protein were also observed with the recombinant protein and likely represent cleavage products. Commercially available antibodies also recognized these molecules. However, the commercially available Abs showed several non-specific bands. Blocking mAbs (B) reduced AGR2-stimulated PDAC cell migration and (C) blocked the survival effects of AGR2, whereas commercial Abs did not. (D) Immunohistochemical analysis on TMA using mAbs developed showed strong labeling of PDAC (indicated by arrow), but normal pancreas was not labeled.

FIGS. 6A-I. In vivo treatment with AGR2/C4.4A antibodies reduced tumor growth and metastasis and improved survival. Tumor growth and metastasis were measured weekly with the IVIS® Imaging System for live animal bioluminescence imaging after injecting luciferin substrate (Xenogen, Alameda, Calif.). The number of mice that survived until the end of the experiment was noted (Percent Surviving). (A,B,G,H) Model 1-AsPC-1-Aggressive Model. Two weeks after the injection of the aggressive AsPC-1 cells, when the tumors weighed less than 0.5 g (as surgically confirmed from a parallel untreated group), mice (n=6) were treated with control IgG or mAbs (5 mg each of AGR2/C4.4A mAb in combination/kg/body weight/twice a week/i.p) and with or without Gem (100 mg/kg body weight/once a week/i.p) until 7 weeks. (A) All mice treated with combined mAbs survived for at least 6 weeks, while all control mice perished within 6 weeks. (B) Tumor volume was estimated weekly by imaging. Combo IgG with and without Gem showed reduction in tumor volume as compared to Control IgG with and without Gem. Tumor weight and metastasis to liver and lung were compared between control and treated groups ex vivo at the end of the experiment. Mice treated with the mAbs showed greatly reduced tumor growth (G) and metastasis incidence (H). Gemcitabine (Gem) had no significant effect either alone or in combination with the mAbs. (C,D) Model 2-Capan2-Stromal Model. Two weeks after the injection of stromal forming Capan-2 cells, mice (n=7) were treated with 15 mg AGR2 or C4.4A mAb/kg/body weight/twice a week/i.p. Treatment was stopped after 15 weeks (13 weeks of treatment) and tumor size in surviving animals was monitored by bioluminescence until 63 weeks. (C) Treatment with either mAb individually showed 24 wk improvement in survival as compared to control mice, which died by nine weeks. Forty-eight weeks past no-treatment, mice showed no tumor re-occurrence. (D) Mean tumor volume changes indicated that mice treated with either mAb showed slower growth. In several mice, tumors were observed to disappear. (E,F) Model 3-Capan-2-Regression Studies. Four weeks after the injection of Capan-2 cells, when tumors weighed more than 1 g (as surgically confirmed from a parallel untreated group), mice (n=5) were treated with AGR2 or C4.4A mAb 15 mg/kg/body weight/twice a week/i.p or with both mAbs in combination (7.5 mg each). Treatment was stopped after 12 weeks. Bioluminescence was monitored on surviving animals until 18 weeks. (E) Treatment of mice possessing tumors larger than 1 g with mAbs improved their survival by 14 wk compared to control mice, which died within 4 wk of treatment. (F) Reduction in tumor volume for each treatment group is shown as measured by bioluminescence imaging. (I) Histological examination of tumors developed in Model 3 was conducted. TUNEL staining of paraffin sections showed increased apoptotic cells in antibody treated groups either alone or in combination compared to control. Staining for p-ERK and Ki-67 showed increased activity in cancer cells of control mice, while antibody treated mice showed no activity in the cancer cells. Quantitation indicated a significant increase in the number of apoptotic cells per field in sections from tumors of mice treated with mAbs (*$p<0.05$).

FIGS. 7A-D. Extracellular rAGR2-mediated functions. (A) Pancreatic cancer cells (BxPC-3 and MiaPaCa-2) were used for these studies. Extracellular addition of rAGR2 caused a significant dose-dependent increase in proliferation (BxPC-3-3-fold increase; MiaPaCa-2-4-fold increase; $p<0.05$). Pancreatic cancer cells were plated ($2 \times 10^4$ cells) with and without rAGR2 (0-100 nM) on a Boyden's chamber for migration studies (B) and on an invasion chamber for invasion studies (C). After 22 h, cells were fixed with methanol and stained by hematoxylin, and cells in 10 random fields at 100× magnification were photographed and counted. Extracellular addition of rAGR2 caused a significant dose-dependent increase in migration (BxPC-3-7-fold increase; MiaPaCa-2-3-fold increase) and invasion (BxPC-3-10-fold increase; MiaPaCa-2-3-fold increase). (D) For analysis of apoptosis, BxPC-3 cells were treated with and without Gem (1 µM) and AGR2 (100 nM). Gem treatment resulted in a significant increase in apoptosis (1-fold). Extracellular addition of rAGR2 significantly reduced the Gem induced apoptosis (50% reduction), thus improving the survival of the cancer cells. Data shown are mean±SE for 3 experiments (*$p<0.05$ vs. control).

FIGS. 9A-D. Silencing C4.4A reduced basal and rAGR2-mediated functions. BxPC-3 pancreatic cancer cells were transiently transfected with SiControl, SiC4.4A, SiCD59, or SiuPAR. (A) For proliferation studies, cells were treated without (basal) and with rAGR2 (100 nM, daily), and cell numbers were estimated by MTS assay after 48 h. The effects of silencing the candidate receptors on migration (B) and invasion (C) were analyzed. C4.4A silencing significantly reduced both basal and rAGR2-stimulated proliferation, migration, and invasion. Silencing of the other candidate receptors had no significant effects. (D) For studies on apoptosis, cells were treated without or with Gem (0.5 µM) and rAGR2 (100 nM). In SiControl-transfected cells, Gem stimulated apoptosis and this effect was ameliorated by the addition of rAGR2. Silencing of C4.4A induced apoptosis in these cells, whereas Gem did not further increase apoptosis. After C4.4A silencing, addition of rAGR2 did not protect the cells from the effects of Gem. Data shown are mean±SE for 3 experiments (*$p<0.05$).

DESCRIPTION OF ILLUSTRATIVE EMBODIMENTS

Figure 2C:
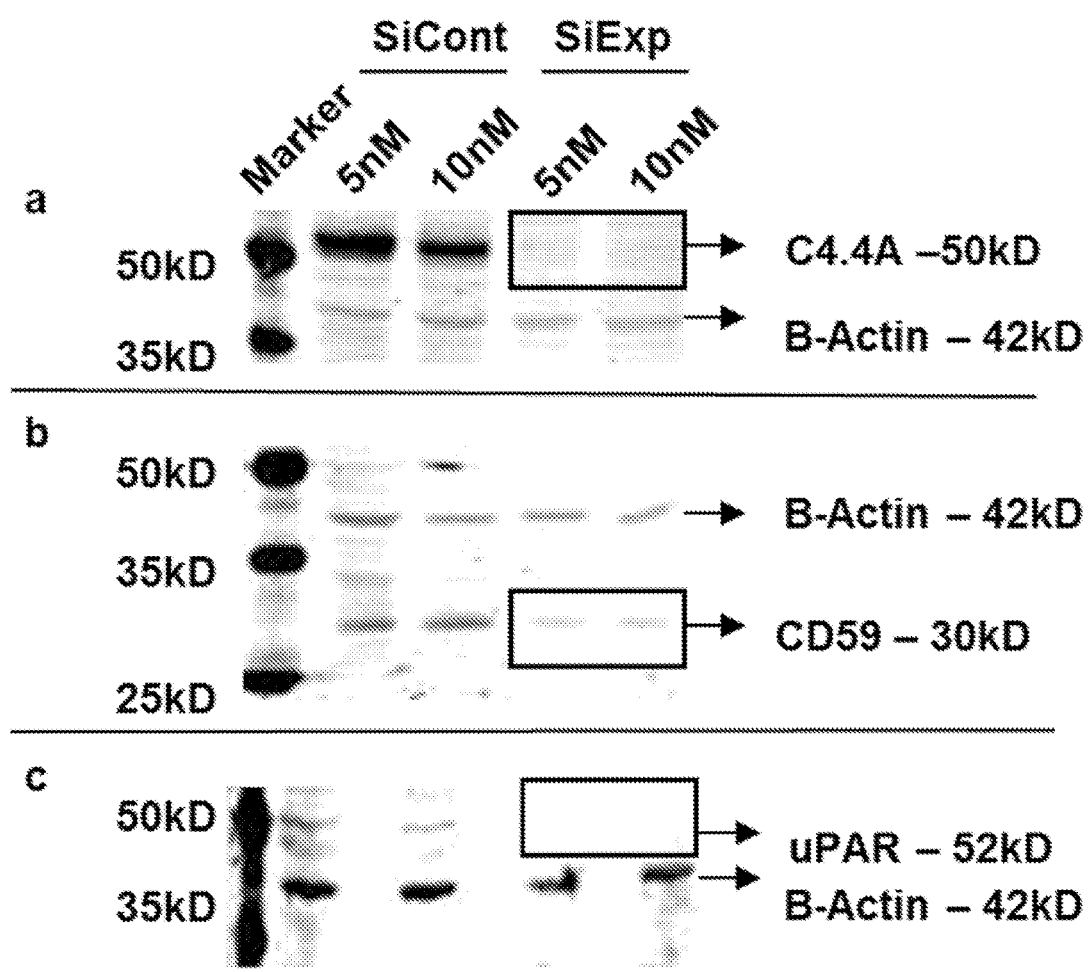

The present invention is based, in part, on the finding that C4.4A (LYPD3) is the functional cell surface receptor for extracellular AGR2. Herein, C4.4A (LYPD3) was identified as the functional cell surface receptor for extracellular AGR2. To support the idea that an AGR2/C4.4A autocrine loop may be a therapeutic target against cancer, monoclonal blocking antibodies against both AGR2 and C4.4A were developed. In vivo treatment with these antibodies significantly reduced PDAC tumor weight and metastasis and prolonged survival. These results suggest that the AGR2/C4.4A interaction is a target with therapeutic potential for cancer therapy.

I. AGR2 and C4.4A

AGR2 is associated with poor outcomes in several tumor types (Brychtova et al., 2011) but the mechanisms have previously been unknown. AGR2 has been reported to be involved in protein maturation and folding (Park et al., 2009; Zhao et al., 2010; Altschul et al., 1997; Higa et al., 2011), to regulate cathepsins (Dumartin et al., 2011), and to modulate MUC-1 levels (Park et al., 2009; Norris et al., 2013). However, these roles of AGR2 do not explain its ability to act as an oncogene (Wang et al., 2008) or the ability of AGR2 to increase the aggressiveness of several types of cancer. It is therefore likely that this protein has multiple intracellular and extracellular functions. Potentially, its physiologic and pathologic roles differ. In the present study, extracellular addition of rAGR2 stimulated the proliferation, migration, invasion, and chemoresistance of PDAC cells. These actions required the presence of cell surface receptors. Thus, based on these data, and without being bound by theory, the role of AGR2 in cancer is mechanistically similar to its roles in amphibians, where it is a secreted signaling molecule that interacts with a specific receptor.

In amphibians, AGR2 promotes limb growth by interacting with Prod1 (Kumar et al., 2007; da Silva et al., 2002), a GPI-linked receptor related to the Ly6 family of receptors in humans (Galat, 2008; Chatterjee and Mayor, 2001). The Lys6 family includes uPAR, C4.4A, and CD59 (Galat, 2008; da Silva et al., 2002). The present study indicated that the Lys family receptors (uPAR, C4.4A, and CD59) were co-immunoprecipitated with AGR2, likely because of the structural homologies between these receptors (Galat, 2008). Nevertheless, only blocking the interaction of AGR2 with C4.4A by silencing or blocking antibodies reduced the endogenous (basal) and extracellular rAGR2-stimulated PDAC cell functions. Though it was reported that in a yeast-two-hybrid system Dystoglycan-1 bound to AGR2, the present co-immunoprecipitation study could not verify this interaction. Surprisingly, it was observed that silencing of other two receptors, CD59 and uPAR, slightly increased the migration of PDAC cells. This observation was unexpected, as a previous report suggested that silencing uPAR inhibited PDAC cell migration (Xue et al., 2009). It is unclear what accounts for this difference, but it may be due to the studies being conducted in different cell lines. Nevertheless, the data shown here support a model in which AGR2 and C4.4A participate in an autocrine loop that activates survival mechanisms.

In previous gene profiling studies, C4.4A was found to be highly expressed in pancreatic cancer but not in normal or chronic pancreatitis tissue (Logsdon et al., 2003). C4.4A is an orphan receptor described previously as a regulator of cancer cell metastasis (Rösel et al., 1998; Jacobsen and Ploug, 2008). C4.4A increases metastasis in melanoma (Rösel et al., 1998) and non-small cell lung cancer (Hansen et al., 2007), and C4.4A protein levels correlate with poor prognosis in breast cancer (Hansen et al., 2007) and colorectal cancer (Paret et al., 2007; Konishi et al., 2010). C4.4A is herein identified as a functional cell surface receptor for AGR2. Silencing or antibody-mediated blocking of C4.4A eliminated the effects of extracellular AGR2, thus supporting AGR2 as the ligand for C4.4A. However, the mechanism of action of C4.4A is had not previously been investigated. Hence, the signaling complex molecules that interact with C4.4A were examined in order to identify specific molecules.

Like other glycosylphosphatidylinositol (GPI)-linked plasma membrane receptors, C4.4A does not have an intracellular domain to mediate downstream signaling mechanisms. On the basis of homologies between C4.4A and uPAR, another member of the Ly6 family, these interactions likely include extracellular matrix proteins and specific integrin receptors. C4.4A is known to promote migration by associating with α6β4 (Ngora et al., 2012). C4.4A was also previously reported to bind laminins 1 and 5, although functional studies were not conducted (Paret et al., 2005). Laminins 1 and 5 are thought to interact primarily with integrin α3β1 (Smith et al., 2001; Higa et al., 2011). Integrin α3β1 is expressed by pancreatic ductal cells (Jiang et al., 2002). Silencing of laminin 1, laminin 5, or integrein β1 abolished the effects of AGR2 treatments, thus suggesting their involvement in the AGR2-mediated C4.4A receptor complex.

To examine the potential therapeutic benefits of blocking the AGR2/C4.4A autocrine loop, blocking mAbs against the ligand (AGR2) and the receptor (C4.4A) were developed. Both Abs blocked basal and AGR2-mediated functions. Pre-clinical studies using the blocking mAbs in three different types of preclinical models resulted in significant reductions in tumor weight and metastasis and improved survival. Treatment with mAbs had better benefits than treatment with Gemcitabine (Gem), the clinical standard of care for PDAC. Partial or complete regression of tumors was observed in several mice after treatment with individual mAb or with the combination of both mAbs. Even several weeks post treatment, no tumor recurrence was observed.

Thus, AGR2 has extracellular functions to increase the aggressiveness of cancer cells and C4.4A is the functional receptor of AGR2. The signaling complex of C4.4A likely includes laminin 1, laminin 5, and β1 integrin. Blocking mAbs against AGR2 and/or C4.4A significantly reduce tumor growth and metastasis, and lead to tumor regression resulting in remarkably improved survival.

II. Therapeutic Antibodies

In certain embodiments, an antibody or a fragment thereof that binds to at least a portion of AGR2 or C4.4A protein and inhibits AGR2/C4.4A binding and its associated use in treatment of diseases are contemplated. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-AGR2 or anti-C4.4A antibody is a monoclonal antibody or a humanized antibody. By known means and as described herein, polyclonal or monoclonal antibodies, antibody fragments, and binding domains and CDRs (including engineered forms of any of the foregoing) may be created that are specific to AGR2 protein or C4.4A protein, one or more of its respective epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

AGR2 and C4.4A mRNA sequences (SEQ ID NOs: 1 and 2, respectively) may be used to produce recombinant proteins and peptides as well known to people skilled in the art. For example, such mRNA sequences could be engineered into a suitable expression system, e.g., yeast, insect cells, or mammalian cells, for production of an AGR2 or C4.4A protein or peptide.

Animals may be inoculated with an antigen, such as a soluble AGR2 or C4.4A protein, in order to produce antibodies specific for AGR2 or C4.4A protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (mAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with an AGR2 or C4.4A antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference. These techniques are further described in: Marks et al. (1992); Stemmer (1994); Gram et al. (1992); Barbas et al. (1994); and Schier et al. (1996).

It is fully expected that antibodies to AGR2 and/or C4.4A will have the ability to block AGR2/C4.4A binding regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacterium containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds AGR2 or C4.4A.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against AGR2 and C4.4A, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. Treatment of Diseases

Certain aspects of the present embodiments can be used to prevent or treat a disease or disorder associated with an AGR2/C4.4A-mediated autocrine survival loop. Functioning of the AGR2/C4.4A autocrine loop may be reduced by any suitable drugs to prevent the AGR2/C4.4A interaction. Preferably, such substances would be an anti-AGR2 or anti-C4.4A antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits the AGR2/C4.4A-mediated autocrine survival loop.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An antibody that binds to AGR2 or C4.4A may be administered to treat a cancer. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; small cell lung cancer; non-small cell lung cancer; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

A. Pharmaceutical Preparations

Where clinical application of a therapeutic composition containing an inhibitory antibody is undertaken, it will generally be beneficial to prepare a pharmaceutical or therapeutic composition appropriate for the intended application.

This will typically entail preparing a pharmaceutical composition that is essentially free of pyrogens, as well as any other impurities that could be harmful to humans or animals. One may also employ appropriate buffers to render the complex stable and allow for uptake by target cells. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired.

The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles, such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

In particular embodiments, the compositions of the present invention are suitable for application to mammalian eyes. For example, the formulation may be a solution, a suspension, or a gel. In some embodiments, the composition is administered via a biodegradable implant, such as an intravitreal implant or an ocular insert, such as an ocular insert designed for placement against a conjunctival surface. In some embodiments, the therapeutic agent coats a medical device or implantable device. The formulation of the invention may be applied to the eye in aqueous solution in the form of drops. These drops may be delivered from a single dose ampoule, which may preferably be sterile and thus render bacteriostatic components of the formulation unnecessary. Alternatively, the drops may be delivered from a multi-dose bottle, which may preferably comprise a device that extracts preservative from the formulation as it is delivered, such devices being known in the art. In other aspects, components of the invention may be delivered to the eye as a concentrated gel or similar vehicle that forms dissolvable inserts that are placed beneath the eyelids.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, or respiratory tract, aerosol delivery can be used. Volume of the aerosol is between about 0.01 mL and 0.5 mL.

An effective amount of the therapeutic composition is determined based on the intended goal. For example, one skilled in the art can readily determine an effective amount of an antibody of the invention to be administered to a given subject, by taking into account factors such as the size and weight of the subject; the extent of the neovascularization or disease penetration; the age, health and sex of the subject; the route of administration; and whether the administration is regional or systemic. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are particular to each individual. Factors affecting the dose include the physical and clinical state of the patient, the route of administration, the intended goal of treatment (e.g., alleviation of symptoms versus cure) and the potency, stability and toxicity of the particular therapeutic substance.

B. Combination Treatments

In certain embodiments, the compositions and methods of the present embodiments involve an antibody or an antibody fragment against AGR2 or C4.4A to inhibit the AGR2/C4.4A interaction, in combination with a second or additional therapy. Such therapy can be applied in the treatment of any disease that is associated with an AGR2/C4.4A-mediated autocrine survival loop. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

```
A/B/A  B/A/B  B/B/A  A/A/B  A/B/B  B/A/A  A/B/B/B
B/A/B/B  B/B/B/A  B/B/A/B  A/A/B/B  A/B/A/B  A/B/B/A
B/B/A/A  B/A/B/A  B/A/A/B  A/A/A/B  B/A/A/A  A/B/A/A
A/A/B/A
```

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. RITUXAN® (Rituximab) is such an example. YERVOY® (ipilimumab; Bristol-Meyers Squibb) is an example of an approved anti-CTLA-4 antibody. KEYTRUDA® (pembrolizumab; Merck) and OPDIVO® (nivolumab; Bristol-Meyers Squibb Company) are examples of approved anti-PD-1 antibodies. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. No. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Kits and Diagnostics

In various aspects of the embodiments, a kit is envisioned containing therapeutic agents and/or other therapeutic and delivery agents. In some embodiments, a kit is contemplated for preparing and/or administering a therapy of the embodiments. The kit may comprise one or more sealed vials containing any of the pharmaceutical compositions of the present embodiments. The kit may include, for example, at least one AGR2 or C4.4A antibody as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Cell lines. NIH 3T3, BxPC3, SU86.86, MiaPaCa-2, AsPC-1 and Capan-2 cells were obtained from ATCC (Manassas, Va.). Cell line identities were verified using DNA fingerprinting (POWERPLEX® 16 System, Promega). Cells were routinely cultured in DMEM containing 10% FBS and were maintained at 37° C. in a humidified atmosphere of 5% $CO_2$.

Antibodies and recombinant proteins. Antibodies were purchase for AGR2 (mouse polyclonal), DAG-1, CD59 (Cat #ab56703, ab105504, ab9182, AbCam, Cambridge, Mass.), laminin 1, laminin 5, ITG β1, α6, β4 (sc-74417, sc-20145, sc-9936, sc-10730, Santa Cruz Biotechnology, Dallas, Tex.), C4.4A, uPAR (Cat #AF5428, MAB807, R&D Systems, Minneapolis, Minn.), p-ERK (Cat #9160, Cell Signaling, Danvers, Mass.), β-actin (Cat #A2066, Sigma, St. Louis, Mo.), and control IgG (Cat #OB010701; Southern Biotech, Birmingham, Ala.). Human and mouse AGR2 proteins have 96% homology (Brychtova et al., 2011), therefore human recombinant (rAGR2) (ab64013, AbCam, Cambridge, Mass.) was used for all studies. Recombinant C4.4A was also purchased (5428-C4-050, R&D Systems, Minneapolis, Minn.).

Transient transfection of siRNA. The following pre-designed and pre-validated siRNAs were purchased from Qiagen (Los Angeles, Calif.): siControl (Cat #1027281), siAGR2 (Cat #SI04274522), siC4.4A (Cat #SI00105700, 707,714,721), siUPAR (Cat #SI03033289), siCD59 (Cat #SI03052616), laminin 1 (α1) (Cat #SI02779511), laminin 5 (β3) (Cat #SI02664116), integrein α6 (Cat # SI02654078), integrein β1 (Cat #SI00300573), integrin β2 (Cat #SI03648848), and integrin β4 (Cat #SI02664109). Cells were transfected with siRNAs (5 or 10 nM) with HIPERFECT® transfection reagent (Cat #301705; Qiagen, Los Angeles, Calif.) and lysates were prepared after 72 h.

IP studies. Commercial AGR2 antibody (2 μg; AbCam) was used to immunoprecipitate AGR2 from SU86.86 lysate (100 μg), and western blotting was conducted. The same membrane was then probed for each antibody individually and with pooled antibodies. In addition, rAGR2 and rC4.4A were suspended together (2 μg each) in lysis buffer and an IP was conducted. IgG (mouse) served as a control. Western blot imaging and processing was performed with an ODYSSEY® imaging system (LI-COR Biosciences, Lincoln, Nebr.).

Cell growth, migration, invasion and apoptosis assays. Wild-type and siRNA transfected PDAC cells were grown with rAGR2 (0-500 nM) in the presence and absence of antibodies (polyclonal commercial or newly developed mAbs) (1 μM). The medium was refreshed daily. Cell numbers were estimated after 48 h by MTS assay as described previously (Ramachandran et al., 2007). In order to avoid the differences in basal values for each cell line, the data are presented as the percent of viable cells compared to the appropriate controls. Migration and invasion assays were conducted at 24 h as described previously (Ramachandran et al., 2007). Apoptosis assays were conducted 72 h after adding Gemcitabine (Gem) to Gem-sensitive BxPC-3 cells (1 μM) and Gem-resistant AsPC-1 cells (5 μM) (Arumugam et al., 2009) as described previously (Ramachandran et al., 2008). Because siRNA transfection itself induced basal apoptosis, cells transfected with siRNAs were treated with a lower concentration of Gem (BxPC3: 0.5 μM; AsPC-1: 1 μM).

Immunohistochemical (IHC) staining. IHC was performed on tissue microarray (TMA) slides with mAbs (1:1000) and developed using the VECTASTAIN® Universal kit (Vector Laboratories, Burlingame, Calif.) as described previously (Ramachandran et al., 2008). Results were blindly evaluated by a pathologist and expression levels were categorized as positive or negative (cytoplasmic staining of >10% or <10% of the tumor cells, respectively) and staining intensity as strong, moderate, or no staining. Apoptotic cells were detected in paraffin sections by fluorescence-labeled TUNEL staining (Promega, Cat #G3250). Activation of the MapK pathway was evaluated by analysis of the levels of p-ERK (Cell Signaling, Cat #9160; 1:1000) and the proliferative index of the cancer cells was measured by Ki-67 staining (Thermo Scientific, Cat #RM-9106-S0; 1:200).

Blocking monoclonal antibody development. Mouse monoclonal antibodies (mAbs) against AGR2 and C4.4A were developed in the Monoclonal Antibody Core of UT MDACC using unconjugated antigenic peptides. Several hybridoma colonies (2400 for each antibody) were screened for target recognition by ELISA using KLH-conjugated peptides. Selected hybridoma colonies were then cloned and screened by ELISA again to select those with the highest affinity. Selected clones were sub-cloned and purified using protein A columns. Validation of antibody specificity, blocking ability, and purity was conducted by western blotting against recombinant and cell lysates proteins, functional screening (apoptosis assay), binding assays (ELISA assay), and analysis of the purity of selected Abs (SDS-PAGE) (as shown in FIGS. 11A-D). In vitro validation experiments with the selected antibodies included inhibition of cancer cell migration and invasion and the ability to increase Gem-induced apoptosis. Top candidate antibodies with high affinity and functional blocking ability, one each against AGR2 and C4.4A, were purified and further used to conduct in vivo experiments. Final selected clones were 28B for AGR2 and 1A for C4.4A. Antibodies were sub-typed as IgG1 for AGR2 and IgG2b for C4.4A. Purified antibodies for in vivo experiments were produced in the monoclonal antibody core.

In vivo studies. In vivo experiments were conducted with athymic nude mice (B6.Cg-Foxn1$^{nu}$/J—female—age 9 weeks) (NCI, Bethesda, Md.) according to the UT MDACC regulatory standards and IUCAC committee approval. Orthotopic tumors were developed with luciferase-labeled cells ($0.25 \times 10^6$). IgG (Cat #OB010701; Southern Biotech, Birmingham, Ala.) served as a control Ab.

Model 1 (AsPC-1-Aggressive Cell Model)—Two weeks after the injection of the aggressive AsPC-1 cells, when the tumors weighed less than 0.5 g (as surgically confirmed from a parallel untreated group), mice (n=6) were treated with control or mAbs (5 mg each of AGR2/C4.4A mAb in combination/kg/body weight/twice a week/i.p) and with or without Gem (100 mg/kg body weight/once a week/i.p) until all of the control mice had died (seven weeks). Tumor weight and metastasis to liver and lung were compared between control and treated groups ex vivo at the end of the experiment.

Model 2 (Capan-2-Stromal Model)—Two weeks after the injection of stroma forming Capan-2 cells, mice (n=7) were treated with 15 mg AGR2 or C4.4A antibody/kg/body weight/twice a week/i.p. Treatment was stopped after 15 weeks (13 weeks of treatment) and tumor size in surviving animals was monitored by bioluminescence until 63 weeks.

Model 3 (Capan2-Regression Studies)—Four weeks after the injection of Capan-2 cells, when tumors weighed more than 1 g (as surgically confirmed from a parallel untreated group), mice (n=5) were treated with AGR2 or C4.4A mAbs at 15 mg/kg/body weight/twice a week/i.p or with both mAbs in combination (7.5 mg each). Treatment was stopped after 12 weeks. Bioluminescence was monitored on surviving animals until 18 weeks. Tumor growth and metastasis were measured weekly with the IVIS® live animal bioluminescence imaging system after injecting luciferin substrate (Xenogen, Alameda, Calif.). The number of mice surviving was recorded each week and shown as the percent of the original group size.

Statistical analysis. All in vitro experiments were conducted in triplicate and carried out on three or more separate occasions. Data presented are the mean of the three or more independent experiments±SEM. In vivo experiments were conducted with groups of 7-10 mice. Statistically significant differences were determined by ANOVA analysis (Newman-Keuls Multiple Comparison Test) and were defined as a p-value of <0.05.

Example 1

Extracellular AGR2 Stimulates PDAC Aggressiveness and Chemoresistance In Vitro

It was previously shown that AGR2 is highly expressed and secreted by PDAC cells and contributes to chemoresistance (Ramachandran et al., 2008). Herein, it was assessed herein whether extracellular AGR2 (rAGR2) mimics the effects of AGR2 expression. Since PDAC cell lines are heterogeneous, multiple cell models were used—BxPc-3 (epithelial phenotype, sensitive to Gem), AsPC-1, and MiaPaCa-2 cells (mesenchymal phenotype, highly resistant to Gem) (Arumugam et al., 2009).

In AsPC-1 cells, treatment with rAGR2 increased proliferation (3-fold), migration (10-fold), and invasion (3-fold) in a concentration-dependent manner (FIGS. 1A-C). Similar effects were observed with BxPC-3 and MiaPaCa-2 cell lines (FIGS. 7A-C). To determine the effects of rAGR2 on cancer cell resistance to therapeutic agents, PDAC cells were treated with Gem in the presence and absence of rAGR2. Although AsPC-1 cells are highly resistant, a significant 3-fold increase in apoptosis was induced at a concentration of 5 µM Gem (FIG. 1D). Simultaneous treatment with rAGR2 reduced the effect of Gem to nearly the control level (>50% reduction), demonstrating a strong survival effect. AGR2 treatment had even larger effects with BxPC3 cells, which are more Gem sensitive (FIG. 7D). Thus, extracellular recombinant AGR2 recapitulated the effects on PDAC cells previously observed with AGR2 expression (Ramachandran et al., 2008).

Example 2

C4.4A is the Functional Receptor for AGR2

Figure 8A:
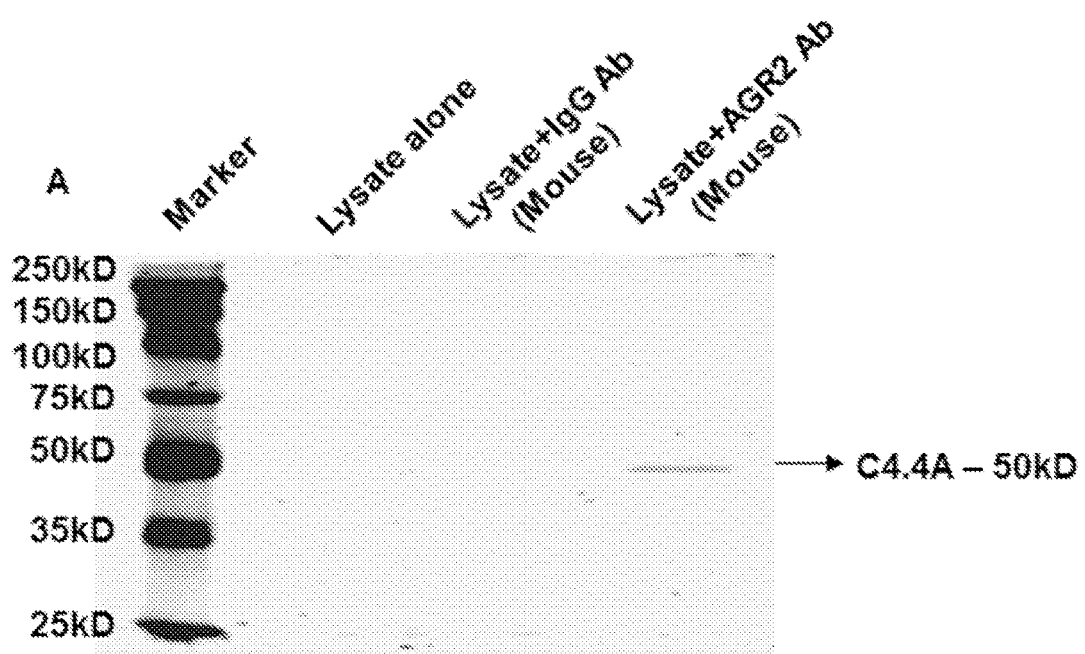
FIGS. 8A-I. Candidate receptor binding and silencing. Western blotting showing the immunoprecipitation of candidate receptors of AGR2: (A) CD59, (B) uPAR and (C) C4.4A. IP analysis was conducted using a commercially available anti-AGR2 antibody, and IgG was used as the control antibody. Immunoprecipitated samples were loaded for western blot analysis, and the gel was probed with respective antibodies. AGR2 IP was co-immunoprecipitated with all three candidate receptors. Lane 1: molecular weight markers; Lane 2: lysate alone; Lane 3: lysate+IgG Ab (mouse); Lane 4: lysate+anti-AGR2 antibody (mouse). Micrograph shown is representative of three independent experiments. (D) Recombinant AGR2 and C4.4A were combined in solution to test for direct physical interaction, and IP was conducted using anti-AGR2 antibody and probed for C4.4A by western blotting. IgG was used as the control antibody. rAGR2 directly interacted with rC4.4A, as indicated by this pull-down experiment. Lane 1: molecular weight markers; Lane 2: recombinant proteins+IgG Ab (mouse); Lane 3: recombinant proteins+anti-AGR2 antibody (mouse). (E) RT-PCR of pancreatic cancer cell lines showed expression of C4.4A in all cell lines tested. The micrographs shown are representative of three independent experiments. (F) Western blot also showed the expression of C4.4A at the protein level in all pancreatic cancer cell line lysates tested. The micrographs shown are representative of three independent experiments. (G-I) Silencing of each candidate receptor was transiently accomplished using siRNA at two final concentrations (5 and 10 nM) in AsPC-1 cells. Western blotting was conducted with respective antibodies, and the same membranes were also blotted with β-actin, which served as loading control. Lane 1: molecular weight markers; Lane 2: SiControl (5 nM); Lane 3: SiControl (10 nM); Lane 4: respective siRNA (5 nM); and Lane 5: respective siRNA (10 nM). Both concentrations of siRNA showed a near-complete silencing of each receptor. The micrograph shown is representative of three independent experiments.
Figure 8B:
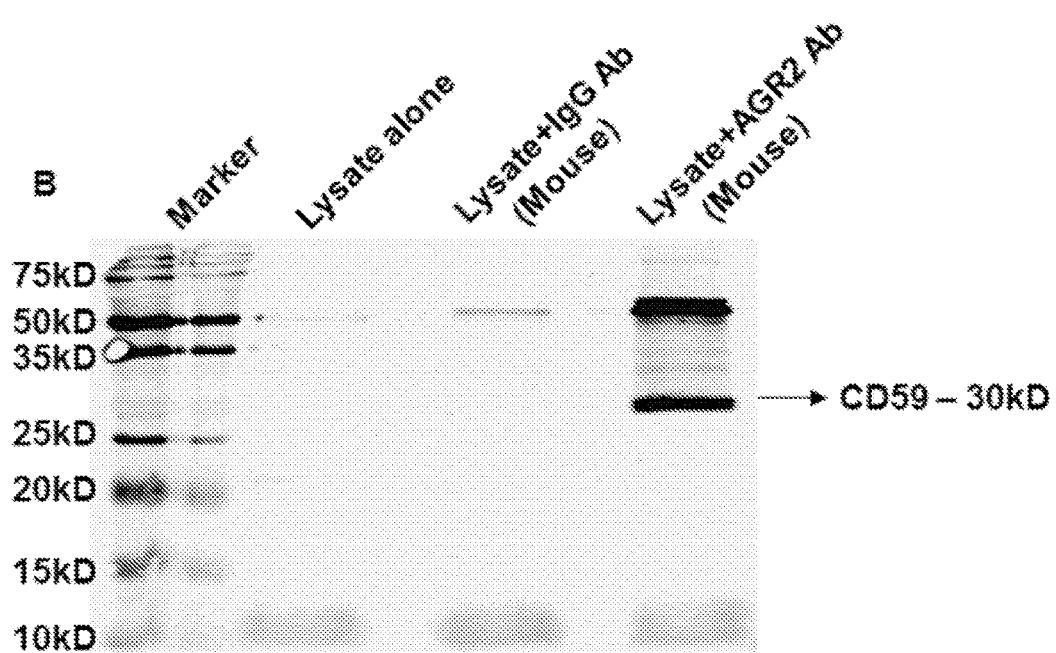
Figure 8C:
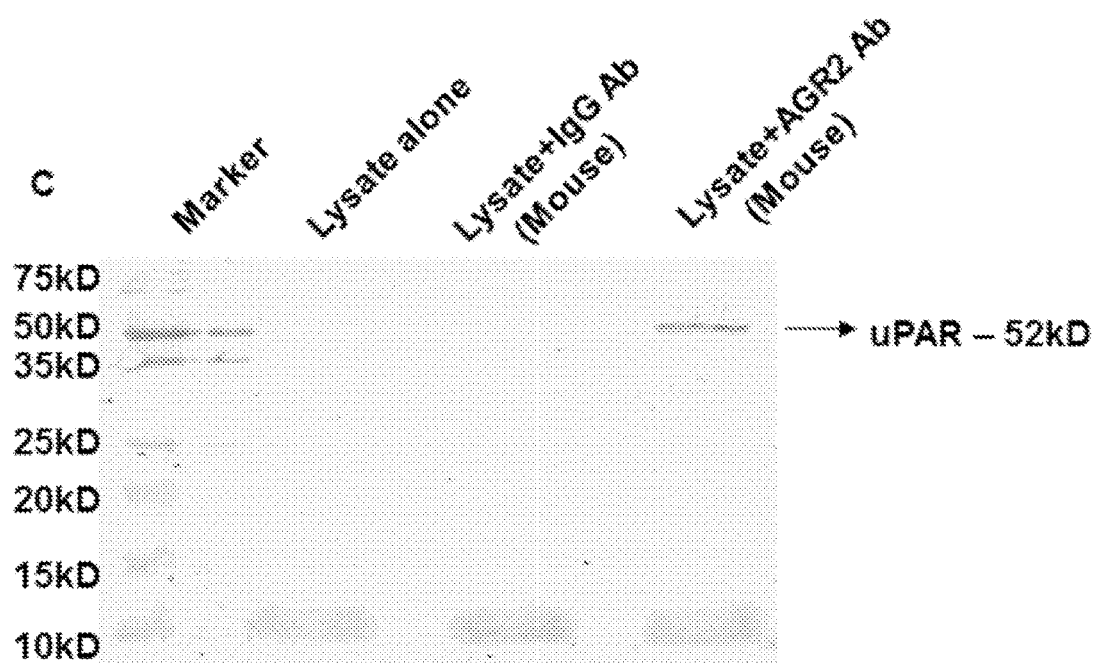

Candidate receptors for AGR2 were selected from the literature and examined for importance in AGR2 functions. The Ly6 receptor family members uPAR, C4.4A, and CD59 co-immunoprecipitated with AGR2 (FIG. 2A), while DAG-1 did not co-immunoprecipitate (FIGS. 8A-C). To determine the functional importance of each receptor, they were silenced using siRNAs and significant silencing was confirmed (FIG. 2C and FIGS. 8G-I). Only silencing of C4.4A significantly reduced basal cell proliferation, migration, and invasion and nearly completely abolished rAGR2-stimulated cell proliferation, migration, and invasion in AsPC-1 cells (FIGS. 3A-C) and BxPC-3 cells (FIGS. 9A-C). On the other hand, silencing of CD59 and uPAR significantly increased AsPC-1 cell migration.

C4.4A silencing also blocked AGR2-mediated chemoresistance to Gem (FIG. 3D and FIG. 9D). Silencing of C4.4A alone, and in combination with Gem, resulted in significantly increased rates of apoptosis (2-fold), which was a greater increase than that observed with Gem treatment of control cells (FIG. 3D). Importantly, the ability of AGR2 treatment to protect cells from Gem was abolished after C4.4A silencing. To control for off-target effects, four siRNA sequences were examined for C4.4A, each of which showed comparable results (FIG. 3E). These data support the idea that the effects of extracellular AGR2 are mediated by interaction with C4.4A.

Figure 8D:
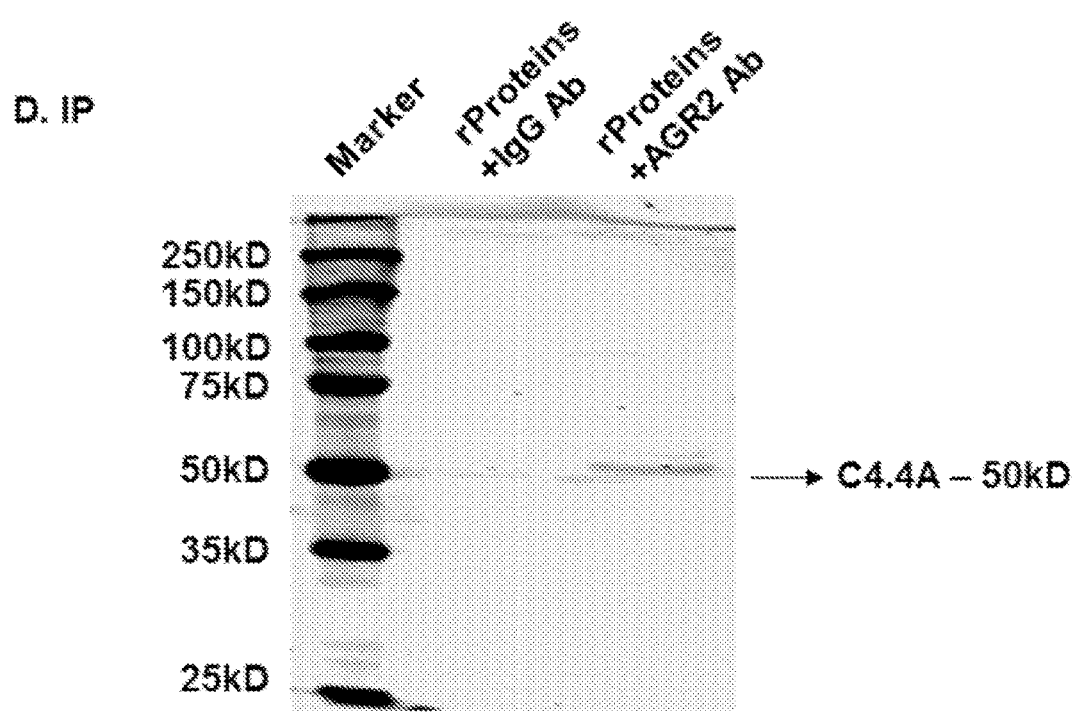
Figure 8E:
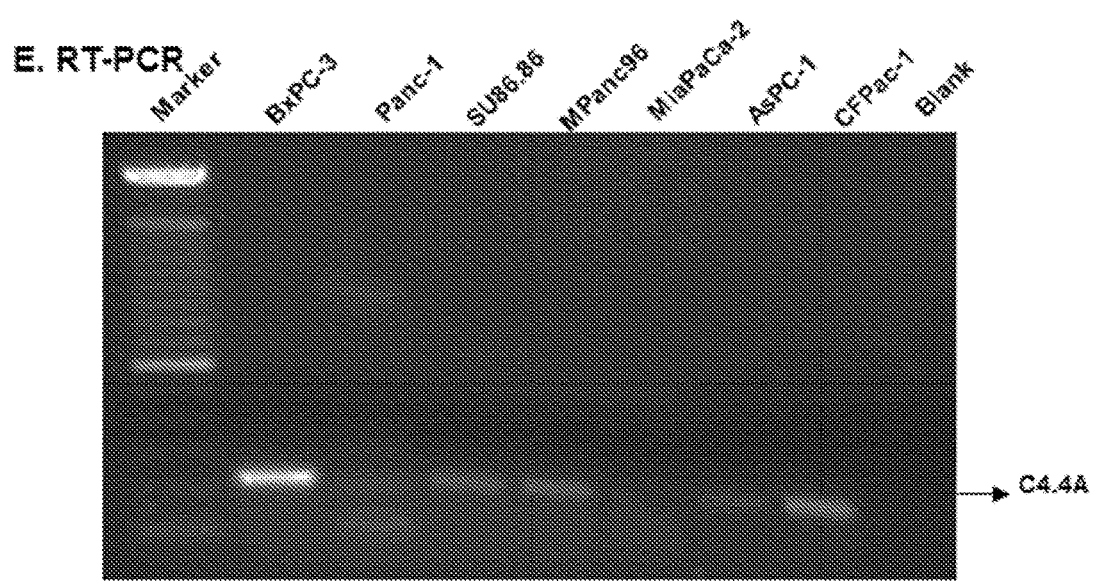
Figure 8F:
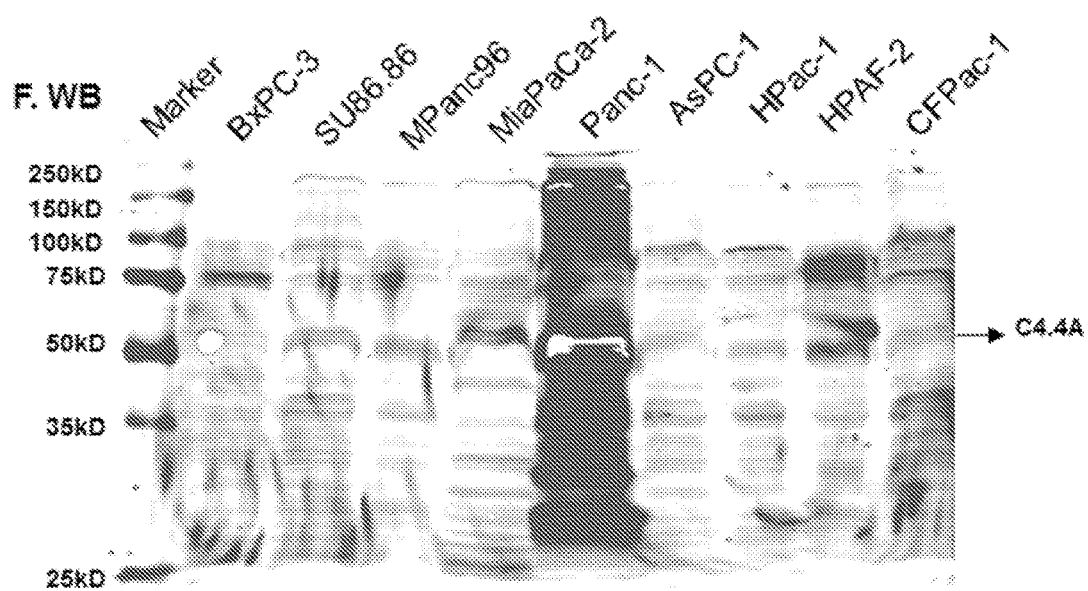
Figure 8G:
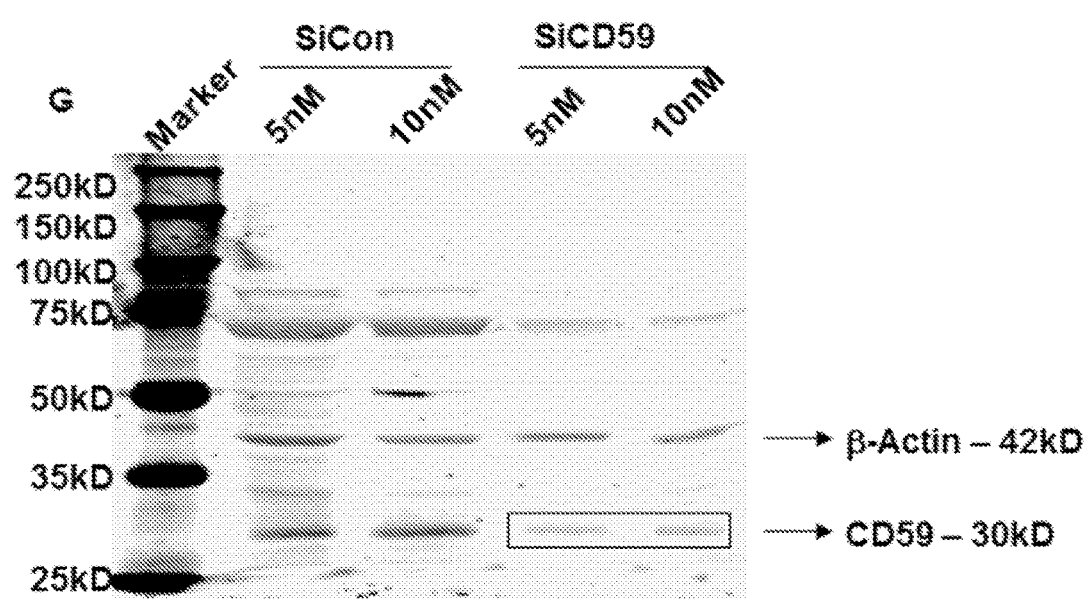
Figure 8H:
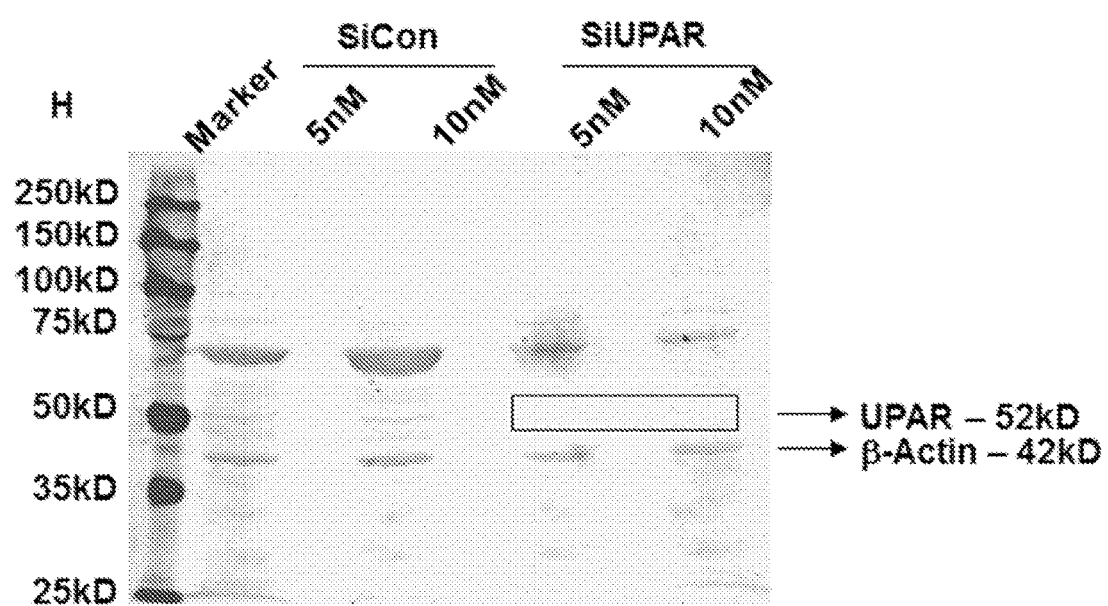
Figure 8I:
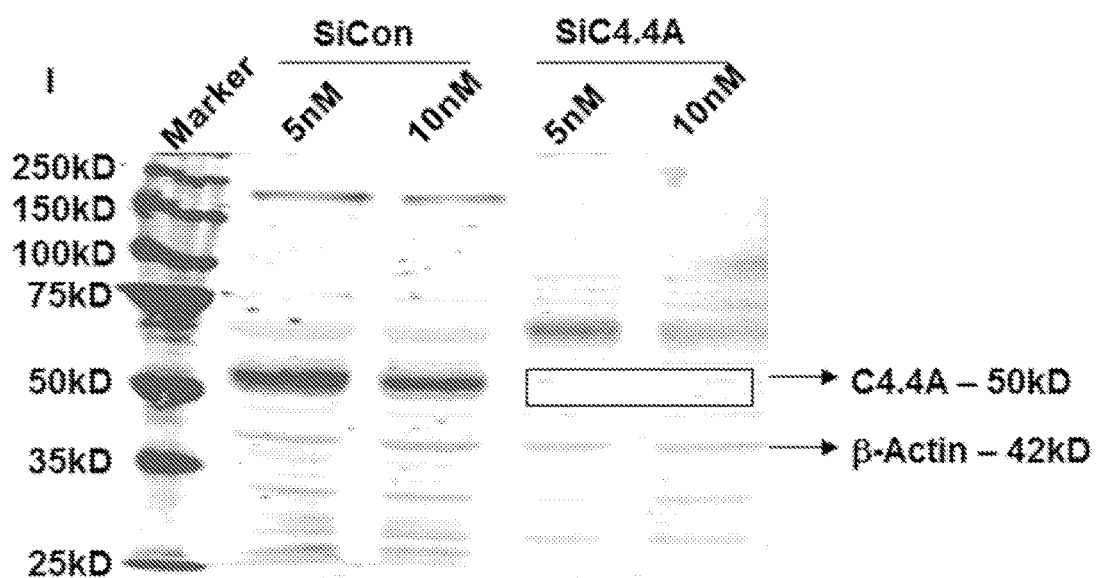

To determine whether AGR2 and C4.4A interact directly or only by association in a complex, rAGR2 and rC4.4A were combined in the absence of other proteins and co-immunoprecipitation was conducted. Direct interaction between rAGR2 and rC4.4A was indicated by the presence of an obvious band in this assay (FIG. 2B). Nine PDAC cell lines were also examined for C4.4A mRNA and protein expression and it was observed that it was present in all lines (FIGS. 8D-F).

Example 3

C4.4A Requires Integrin β1 and Laminins 1 and 5 for Activity

Figure 4A:
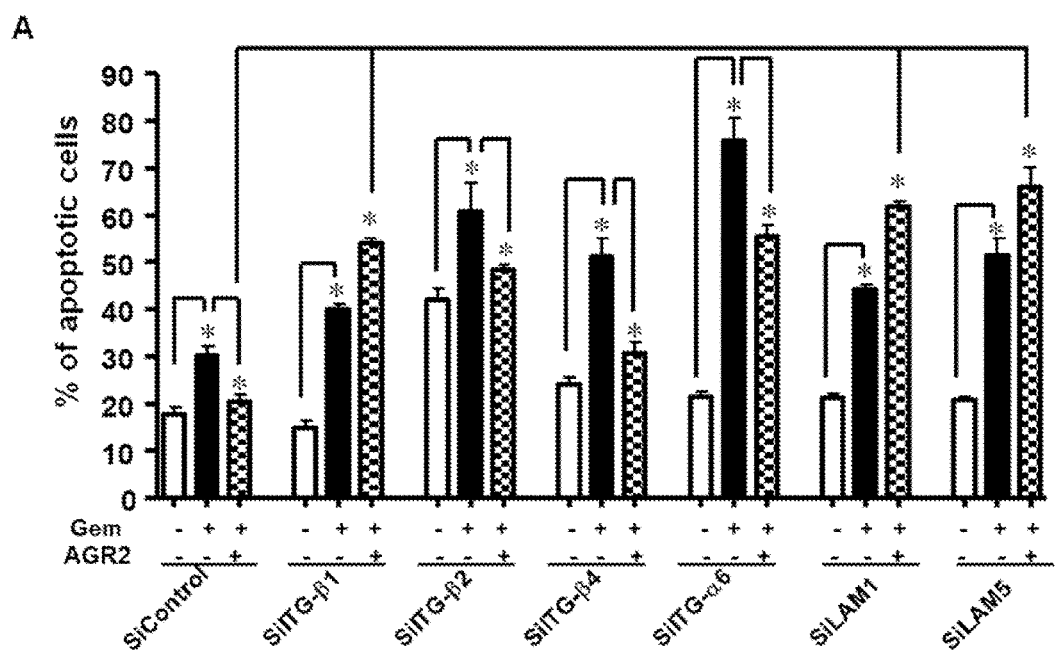
FIGS. 4A-C. Effects of AGR2 are mediated by C4.4A interacting with integrin β1 and laminin 1 or laminin 5. (A) In SiControl AsPC-1 cells, Gem addition stimulated apoptosis and addition of rAGR2 inhibited this effect. AsPC-1 cells were also transfected with siRNAs against ITG-β1, ITG-β2, ITG-β4, ITG-α6, laminin 1, and laminin 5 Only silencing of laminins 1 and 5 and integrin β1 increased Gem-stimulated apoptosis and abolished the survival effects of AGR2. (B) Silencing of laminins 1 and 5 and integrin β1 by siRNA significantly abolished AGR2-mediated proliferation of AsPC-1 cells. (C) Commercially available blocking antibodies to ITG-β1, ITG-β2, ITG-β4, ITG-α6, laminin 1, and laminin 5 showed similar results as the siRNA treatments with only Abs to laminins 1 and 5 and integrin β1 blocking AGR2-mediated survival effects. Data shown are mean±SEM for 3 experiments ($*p<0.05$)
Figure 4B:
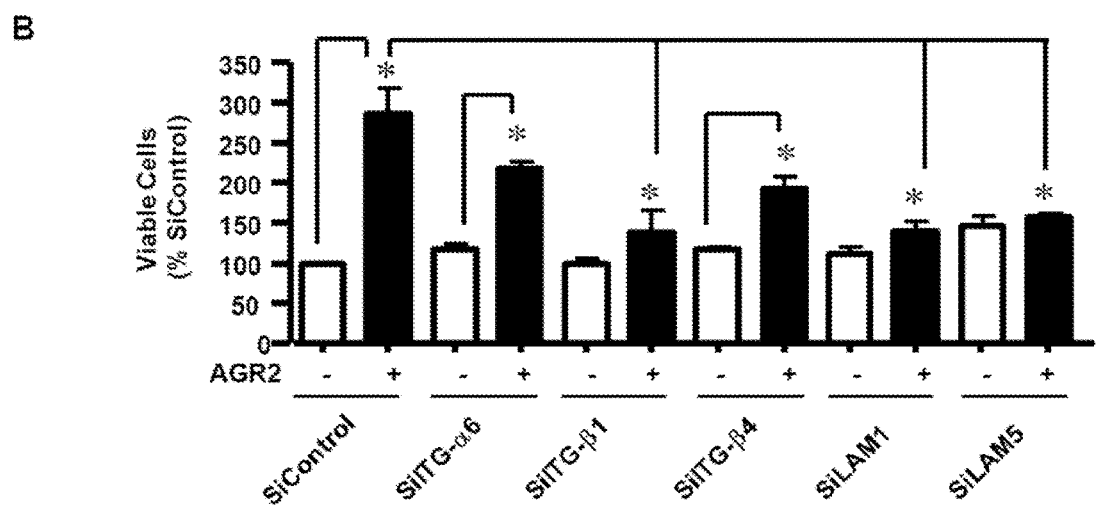
Figure 4C:
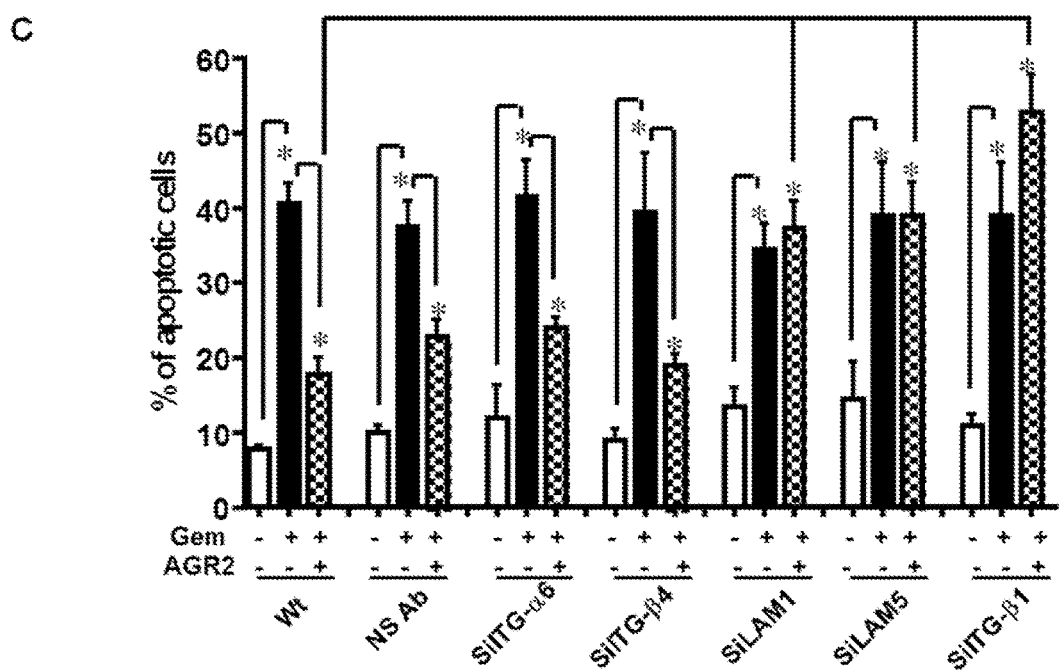
Figure 10A:
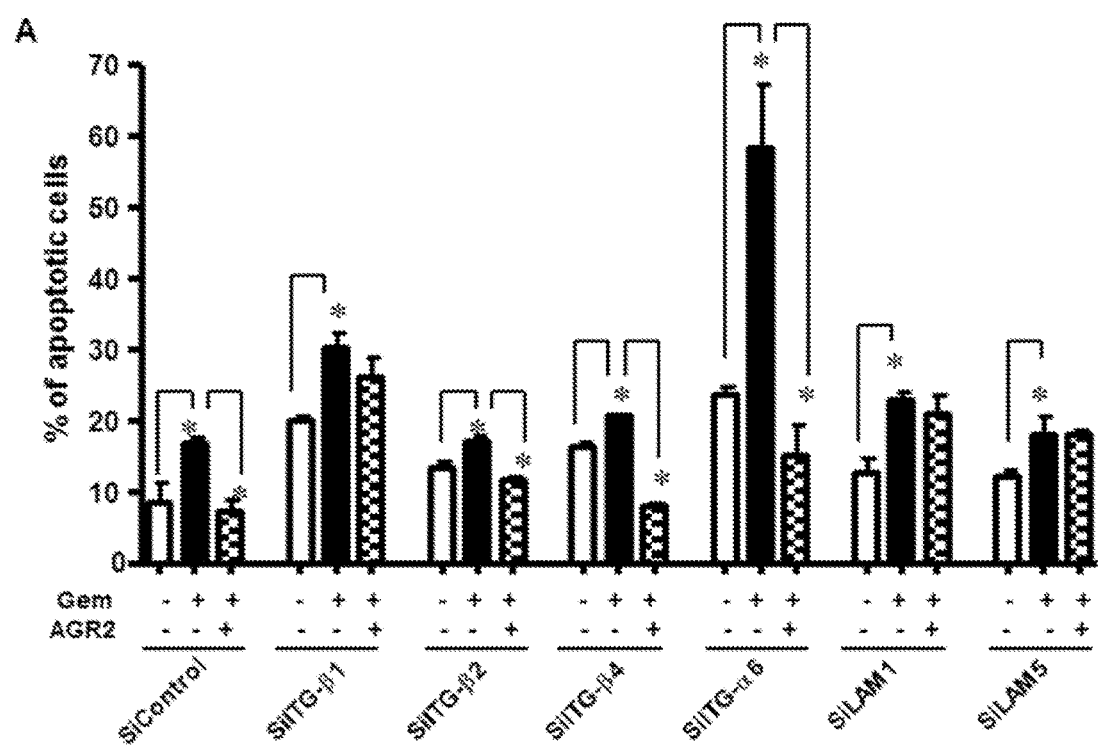
FIGS. 10A-B. Effects of AGR2 are mediated by C4.4A interacting with integrin β1. The role of various integrins was tested as part of the AGR2-C4.4A signaling complex by using a panel of siRNAs. (A) For apoptosis studies, siRNA-transfected BxPC-3 cells were treated without or with Gem (0.5 µM) and AGR2 (100 nM). In SiControl-transfected cells, rAGR2 addition reduced Gem-mediated apoptosis. In contrast, when integrein β1 was silenced, Gem stimulated apoptosis but this effect was not reduced by AGR2. Silencing of other integrins did not have any noticeable effects on abolishing AGR2-mediated survival effects. Because laminins 1 and 5 are known to interact with C4.4A, the silencing effects of these laminins on C4.4A-mediated AGR2 survival effects were assessed. Silencing of laminins 1 and 5 abolished the AGR2-mediated survival effects. (B) To determine the effects of silencing of integrein β1 on AGR2-stimulated cell proliferation, cells were treated with different siRNAs and allowed to grow for 48 h before being analyzed with the MTS assay. Silencing of laminins 1 and 5 and integrein β1 abolished the AGR2-mediated proliferation. Data shown are mean±SE for 3 experiments (*p<0.05).
Figure 10B:
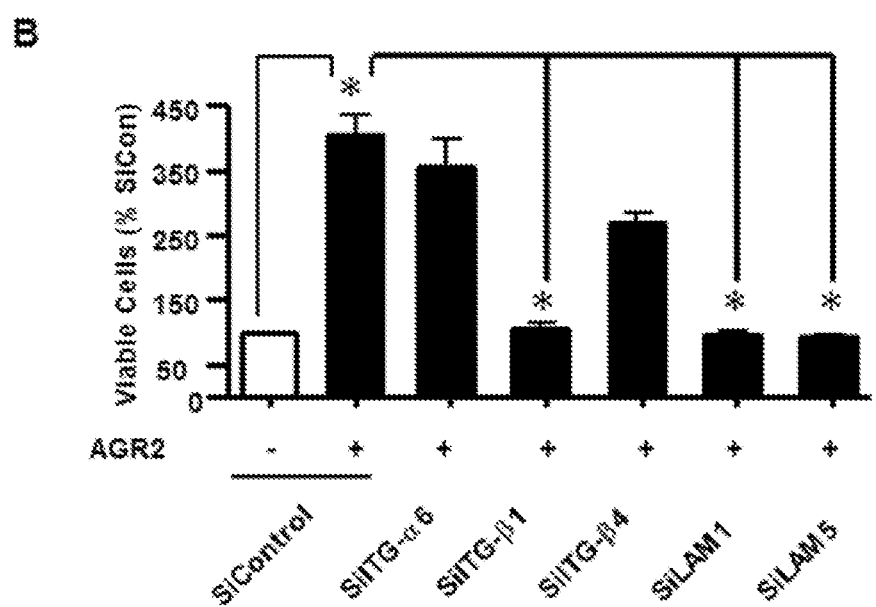
Figure 11A:
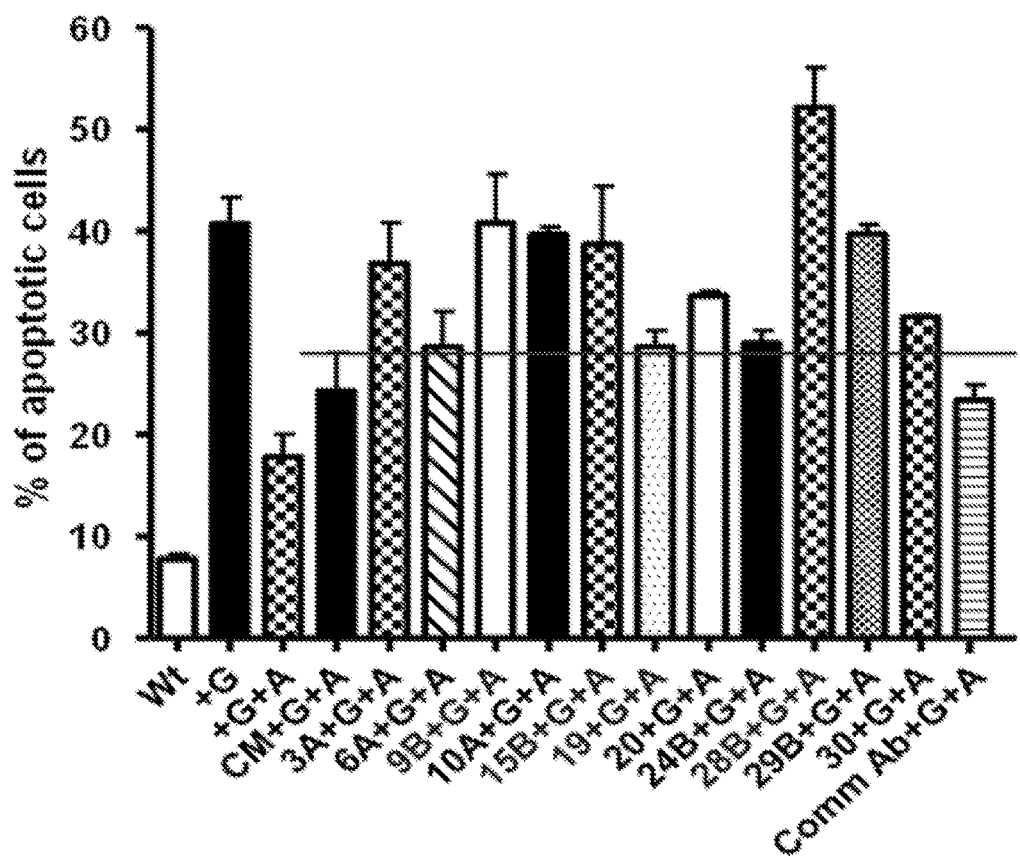
FIGS. 11A-D. Monoclonal antibodies developed bind respectively to AGR2 and C4.4A proteins and blocked their functions. From the endogenous lysate (SU86.86/Panc-1), AGR2 (18 kD) and C4.4A (50 kD) were identified by a panel of mAbs. However, the commercial Abs showed non-specific bands. Extra bands identified with the endogenous protein were re-confirmed with the recombinant protein. For apoptosis studies, AsPC-1 cells were treated without or with Gem (0.5 µM) and rAGR2 (100 nM) and with purified (A) AGR2 and (B) C4.4A Abs (1 µM). Commercially available Abs served as control. Gem addition resulted in increased apoptosis, while, AGR2 addition resulted in survival benefits. Horizontal line represents median apoptotic value. Data shown are mean±SE for 3 experiments (*p<0.05). (C,D) Binding assays were conducted with purified (C) AGR2 and (D) C4.4A Abs as selected from the apoptosis assay as having high blocking efficiency. ELISA assays were conducted by coating antigenic peptide (0.5 µg) and probed with respective purified Abs. Data shown are mean±SE for 3 experiments (*p <0.05). Based on high specificity and binding, clone 28B for AGR2 and 1A for C4.4A were selected. Purified Abs were also run on 4-20% gradient gel to check for the presence of heavy (50 kD) and light chains (25 kD). AGR2 and C4.4A Abs showed no extra bands.
Figure 11B:
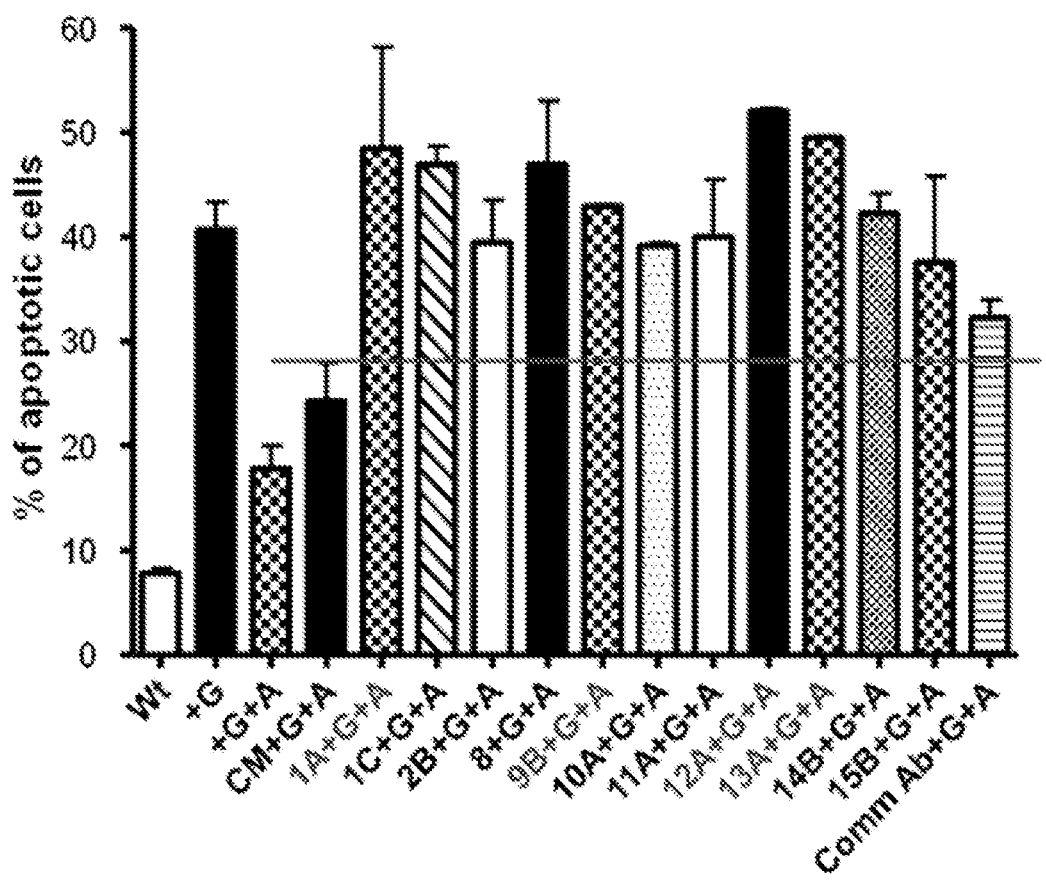
Figure 11C:
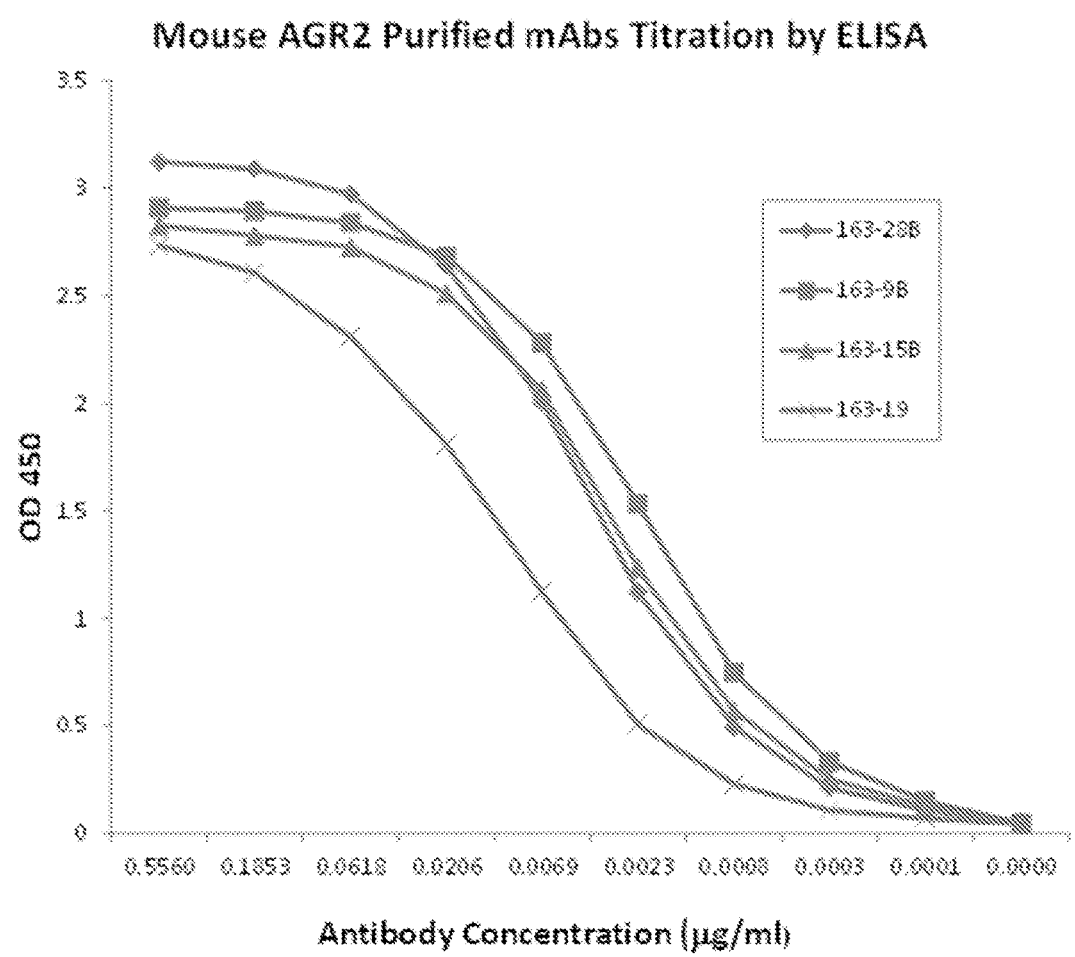
Figure 11D:
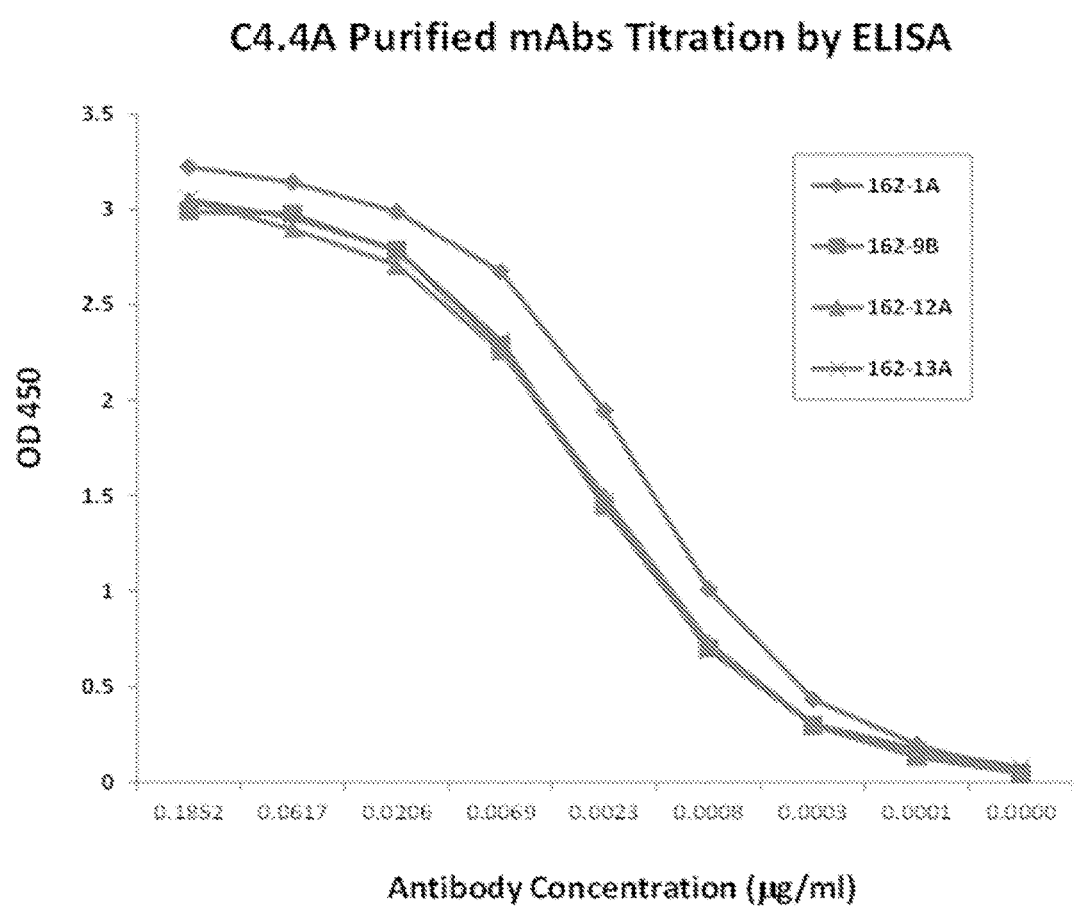

In light of previously identified signaling complexes of uPAR, a member of this receptor family (Smith and Marshall, 2010), surface receptors were investigated, including integrins and extracellular matrix components that might be involved in C4.4A signaling. C4.4A was reported to bind laminins 1 and 5 although the functional consequences were unknown (Paret et al., 2005). Hence, candidate integrins and laminins 1 and 5 were silenced and AGR2-mediated Gem-resistance effects were assessed. Silencing of laminin 1, laminin 5, or integrein β1 completely abolished the protective effects of AGR2, while silencing of integrin β2, β4, or α6 had no effect (FIG. 4A). Similarly, commercial blocking antibodies to laminin 1, laminin 5, and integrein β1 also abolished AGR2 mediated stimulation of proliferation and chemoprotective effects (FIGS. 4B-C). Similar results for the BxPC-3 cell line are shown in FIGS. 10A-B. Taken together these data suggest that laminins 1 and 5 and integrein β1 are involved in the AGR2/C4.4A receptor complex.

Example 4

Developed AGR2 and C4.4A Monoclonal Antibodies Are Highly Specific and Block the Binding of AGR2 to C4.4A To further understand the roles of AGR2 and C4.4A in cancer, their interactions were blocked using antibodies. Commercially available antibodies, while recognizing AGR2 (18 kD) and C4.4A (50 kD) (FIG. 5A), did not block AGR2-induced cell migration (FIG. 5B) or Gem resistance (FIG. 5C). Therefore, AGR2 and C4.4A mAbs (163-28B-1 and 162-1A-1, respectively) were developed that recognized their respective antigens and blocked their interactions (FIG. 5A). Unconjugated antigenic peptides against AGR2 (CIH-HLDESPHSQALKKVFAENKEIQKLAEQ; SEQ ID NO: 3) and C4.4A (CPVRPTSTTKPMPAPTSQTPRQGVE-HEASRDEEPRL; SEQ ID NO: 4) along with adjuvant were injected into Balb/C mice subcutaneously for six weeks. Spleens were harvested and fused with myeloma cells (SP2/0-Ag14) and hybridomas were screened by ELISA using KLH-conjugated peptides. Candidate hybridomas were identified by checking their binding efficiency towards the antigen by Western blot analysis. Both antibodies showed the respective binding of their recombinant and endogenous proteins as compared to commercially available antibodies (FIG. 5A). The novel mAbs were more specific than the commercial antibodies, as indicated by the lack of non-specific bands in Western blots of pancreatic cancer cell lysates. Further purification of the hybridomas was conducted using protein A columns and purified proteins were tested for functional blocking assays. The novel mAbs blocked AGR2 stimulation of cell migration and resistance to Gem while the commercially available antibodies were without effects (FIGS. 5B-C). Migration assays were conducted and basal and AGR2-mediated stimulation in migration was abolished on addition of both the blocking antibodies (163-28B-1 and 162-1A-1) as compared to non-specific antibody, while commercially available AGR2 and C4.4A antibodies did not block the functions of AGR2. Apoptosis assays were conducted in AsPC-1 cells. AGR2 and C4.4A antibodies (163-28B-1 and 162-1A-1, respectively) abolished the AGR2-mediated survival effects thus improving apoptosis, while non-specific antibody and commercially available AGR2 and C4.4A antibodies did not do so.

Example 5

AGR2/C4.4A Are Widely Expressed in Pancreatic Cancer

The expression patterns of AGR2 and C4.4A were also assessed in patient tissues (TMA—Tissue Micro Array) using the mAbs developed (FIG. 5D). Both antibodies showed strong labeling of PDAC, but normal pancreas was not labeled. For AGR2, 105 of 140 (75%) were positive with respective staining of 46% (high), 29% (moderate), and 25% (no staining). High levels of AGR2 expression was associated with higher frequency of lymph node metastasis in overall patient population and in stage II patients ($p<0.05$). There was also weak correlation between the AGR2 expression and differentiation. For C4.4A, 67 of 74 (91%) were positive with respective staining of 52% (high), 39% (moderate), and 9% (no staining). These data confirm that AGR2 and C4.4A are both highly expressed in advanced PDAC. Both molecules tend to be expressed together as the correlation between the expression of AGR2 and C4.4A in PDAC patients was significant ($p<0.0001$, correlation coefficient 0.74 (Spearman r)).

Example 6

Inhibition of the AGR2/C4.4A Autocrine Loop Provides Potential Therapeutic Benefits To evaluate the potential therapeutic benefits of inhibiting the AGR2/C4.4A autocrine loop, the effects treatments with the blocking mAbs have in pre-clinical models were tested. In the aggressive cell model (Model 1) (FIGS. 6A-B), AsPC-1, a highly tumorigenic, metastatic and Gem-resistant cell line, was used. The effect of the combination of both mAbs with and without Gem was tested. Mice were injected orthotopically with luciferase-expressing AsPC-1 cells and tumors were allowed to form for two weeks prior to the start of treatments. After four weeks of treatment (six weeks total), all mice in the control Ab group had died and the other mice were sacrificed to compare tumor weights and metastasis. At that time, 30% of the mice treated with the control Ab in combination with Gem, 100% of the mice with the combination of AGR2 and C4.4A mAbs (163-28B-1 and 162-1A-1, respectively), and 80% of the mice with the combination of mAbs and Gem remained alive. The experiment was terminated at the end of seven weeks. Compared with control Ab, combined mAb treatment reduced tumor weight by 33% ($p<0.03$), and incidence of metastasis by 66% ($p<0.05$) (FIGS. 6G-H). Combining Gem with the mAbs did not have a significant advantage, as this combination resulted in a reduction in tumor weight by 40% ($p<0.003$) and incidence of metastasis by 50% ($p<0.05$). As no substantial benefits were obtained in combination with Gem treatment in Model 1, Gem treatment was not considered in Models 2 and 3. The treatment with the mAbs did not reduce the animal's body weight as compared to control Ab-treated mice, suggesting a lack of systemic toxicity associated with blocking this pathway.

In the stromal model (Model 2) (FIGS. 6C-D), Capan-2, a Gem resistant, dense stroma forming but not metastasizing cell line was used. Mice in the control Ab group all died within nine weeks (seven weeks of treatment) (FIG. 6C). At that time, 43% of mice treated with the AGR2 mAb (163-28B-1) and 57% of mice treated with the C4.4A mAb (162-1A-1) were surviving. Treatments were discontinued after 15 weeks (13 weeks of treatment) and the animals were allowed to survive until they died or were severely morbid. Median survival (the point at which 50% of the animals survived) was six weeks for the control Ab, nine weeks for the AGR2 Ab, and 10 weeks for the C4.4A mAb ($p<0.05$). Both AGR2 and C4.4A Ab treatments reduced the tumor volume by 50% compared to control Ab ($p<0.05$) (FIG. 6D). Some mice (1/7 of AGR2 mAb treated; 3/7 of C4.4A mAb treated) showed complete tumor regression as indicated by bioluminescence imaging and confirmed by surgical examination. After week 63, one mouse was surviving in each of the AGR2 Ab and C4.4A Ab groups. After sacrifice, these animals were examined and no evidence of tumor was observed.

Figure 6I:
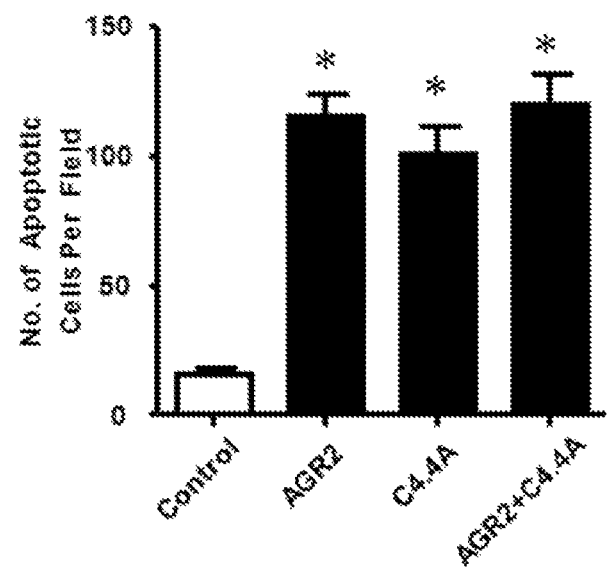

Regression studies (Model 3) were conducted on mice beginning five weeks after cancer cell implantation when tumors were more than 1 g (FIGS. 6E-F). In this study, all mice in the control Ab group died three weeks after initiation of treatment (8 weeks total). At that time, 60% of each mAb treated group survived. Treatment with mAbs was discontinued after 12 weeks and the mice were allowed to survive until they died or were severly morbid. Median survival times were eight weeks for control Ab treated animals, 12 weeks for AGR2 or C4.4A mAb-treated animals, and 11 weeks for animals treated with the combination of AGR2 and C4.4A mAbs ($p<0.05$). The reduction in tumor volume as measured every week by bioluminescence imaging is shown for this model (FIG. 6F). One of five mice treated with the AGR2 mAb showed complete regression of its tumor. Analysis of the residual tumor in surviving mice indicated a high level of apoptotic cells in mAb treated groups (FIG. 6I). Analysis of p-ERK levels indicated that activity of this pathway was completely abolished in antibody treated groups. Analysis of the proliferation indicator, Ki-67 showed no staining on mAb treated groups. Similar results were observed in other PDAC cell models.

Example 7

Sequencing of VH and VL Regions of the 162-1A-1 and 163-29B-1 Monoclonal Antibodies Cell Culture. 162-1A-1 and 163-28B-1 hybridoma cells were grown in RPMI-1640 media containing 10% fetal bovine serum (FBS; HyClone, Logan, Utah), 1 mM sodium pyruvate (Mediatech, Herndon, Va.) and 1× penicillin-streptomycin mix (HyClone) at 37° C. in a 7.5% $CO_2$ incubator.

Isotyping. Isotype of mouse monoclonal antibody produced by each of 162-1A-1 and 163-28B-1 hybridoma cells was determined by ELISA as follows. An ELISA plate was coated with 100 µL/well of one of the following five goat polyclonal antibodies (all from SouthernBiotech, Birmingham, Ala.), 1/1,000-diluted in PBS, at 4° C. overnight:

1. Anti-mouse IgG, γ chain-specific
2. Anti-mouse IgG, γ1 chain-specific
3. Anti-mouse IgG, γ2a chain-specific
4. Anti-mouse IgG, γ2b chain-specific
5. Anti-mouse IgM, µ chain-specific After washing wells with Wash Buffer (PBS containing 0.05% Tween 20), blocking with 300 µL/well of ELISA Buffer (PBS containing 2% Skim Milk and 0.05% Tween 20) for 30 min at room temperature, and washing with Wash Buffer, 100 µL/well of 1:1 mixture of ELISA Buffer and culture supernatant of each hybridoma was applied in duplicate to the ELISA plate. After incubating the ELISA plate for 1 h at room temperature and washing with Wash Buffer, bound antibodies were detected using 100 µL/well of one of the following two goat polyclonal antibodies (both from SouthernBiotech), 1/1,000-diluted in ELISA buffer for 30 min at room temperature:

A. HRP-conjugated goat anti-mouse kappa chain polyclonal antibody
B. HRP-conjugated goat anti-mouse lambda chain polyclonal antibody After washing with Wash Buffer, color development was performed by adding 100 µL/well of ABTS® substrate (AMRESCO, Solon, Ohio) and stopped by adding 100 µL/well of 2% oxalic acid. Absorbance was read at 405 nm.

The result of isotyping was 162-1A-1: IgG2b/kappa and 163-28B-1: IgG1/kappa.

Cloning and sequencing of mouse immunoglobulin variable region genes. Total RNA was extracted from approximately 5×10⁶ of each of 162-1A-1 and 163-28B-1 cells using TRIZOL® reagent (Invitrogen, Carlsbad, Calif.) according to the supplier's protocol. Oligo dT-primed cDNA for 5'-RACE was synthesized using the SMARTER™ RACE cDNA Amplification Kit (Clontech, Mountain View, Calif.) following the supplier's protocol. The variable region cDNAs for heavy and light chains were amplified by polymerase chain reaction (PCR) with PHUSION® DNA polymerase (New England Biolabs, Beverly, Mass.) using 3' primers that anneal specifically to the mouse heavy and light chain constant regions, and the 5'-RACE primer (Universal Primer A Mix) provided in the SMARTER™ RACE cDNA Amplification Kit.

For PCR amplification of heavy chain variable region (VH), the 3' primers have the sequences shown below:

```
                                        (SEQ ID NO: 5)
MCG1:   5'-GCCAGTGGATAGACAGATGG-3' (for γ1 chain)

(SEQ ID NO: 6)
MCG2B:  5'-GCCAGTGGATAGACTGATGG-3' (for γ2b chain)
```

For PCR amplification of kappa light chain variable region (VL), the 3' primer has the sequence shown below:

```
                                        (SEQ ID NO: 7)
MCK:    5'-GATGGATACAGTTGGTGCAGC-3'
```

The amplified VH and VL cDNAs were subcloned into the pJet1.2 vector (Thermo Scientific, Rockford, Ill.) for sequence determination. DNA sequencing was carried out at Tocore (Menlo Park, Calif.) with the following two primers:

```
                                        (SEQ ID NO: 8)
JetFwd: 5'-CGACTCACTATAGGGAGAGCGGC-3'

(SEQ ID NO: 9)
JetRev: 5'-AAGAACATCGATTTTCCATGGCAG-3'
```

Several heavy and light chain clones were sequenced and unique sequences homologous to typical mouse heavy and light chain variable regions were identified. The consensus cDNA sequence for each V gene was obtained with at least four independent clones.

Sequences of VH and VL genes. Amino acid sequences of the VH and VL regions of 162-1A-1 and 163-28B-1 monoclonal antibodies are shown in Table 1. The sequences of CDRs 1, 2 and 3 according to the definition of Kabat et al. (1991) are underlined with a solid line.

TABLE 1

Antibody sequences.

| | Heavy Chain Sequence | | | Light Chain Sequence | | |
|---|---|---|---|---|---|---|
| mAb | CDR1 | CDR2 | CDR3 | CDR1 | CDR2 | CDR3 |
| | Amino acid sequence | | | Amino acid sequence | | |
| | IgG2b/kappa | | | | | |
| 162-1A-1 | SYTMS (SEQ ID NO: 12) | SISSGGGNT YYADSVKG (SEQ ID NO: 13) | SYYYGISY DTY (SEQ ID NO: 14) | RSSQNLVH SDGNTYLH (SEQ ID NO: 15) | KVSNRFS (SEQ ID (NO: 16) | SQSTHVPY T (SEQ ID NO: 17) |
| | MNFGLSLIFLVLILKGVQCEVMLVESG GGLVKPGGSLKLSCAASGFTFS<u>SYTMS</u> WVRQTPEKRLEWVA<u>SISSGGGNTYYAD SVKG</u>RFTMSRDNAKNNLYLQMSSLRSE DTALYYCAR<u>SYYYGISYDTY</u>WGQGTLV TVSA | | | MKLPVRLLVLMFWIPASNSDVVMTQTP LSLPVSLGDQASISC<u>RSSQNLVHSDGN TYLH</u>WYLQKPGQSPKLLIY<u>KVSNRFSG</u> VPDRFSGSGSGTDFTLKISRVEAEDLG VYFC<u>SQSTHVPYT</u>FGGGTKLEIK | | |

TABLE 1-continued

Antibody sequences.

| mAb | Heavy Chain Sequence | | | Light Chain Sequence | | |
|---|---|---|---|---|---|---|
| | CDR1 | CDR2 | CDR3 | CDR1 | CDR2 | CDR3 |
| | Amino acid sequence | | | Amino acid sequence | | |
| | IgG1/kappa | | | | | |
| 163-28B-1 | NYGMN (SEQ ID NO: 20) | WINTDTGKP TYTEEFKG (SEQ ID NO: 21) | VTADSMDY (SEQ ID NO: 22) | RSSQSLVH KVSNRFS SNGNIYLH (SEQ ID NO: 23) | KVSNRFS (SEQ ID NO: 24) | SQSTHVPL T (SEQ ID NO: 25) |
| | MDWLWNLLFLMAAAQSIQAQIQLVQSG PELKKPGETVKISCKASGYTFT<u>NYGMN</u> WVKQAPGKGLKWMG<u>WINTDTGKPTYTE EFKG</u>RFAFSLATSASTAYLQINNLRNE DTATYFCGR<u>VTADSMDY</u>WGQGTSVTVS S | | | MKLPVRLLVLMFWIPASSSDVVMTQTP LSLPVSLGDQASISC<u>RSSQSLVHSNGN IYLH</u>WFLQKPGQSPKLLIY<u>KVSNRFS</u>G VPDRFSGSGSGTDFTLKISRVEAEDLG VYFC<u>SQSTHVPL</u>TFGAGTKLELK | | |

Example 8

Regression Study—Survival Curve in Capan-2 Tumors

Figure 12:
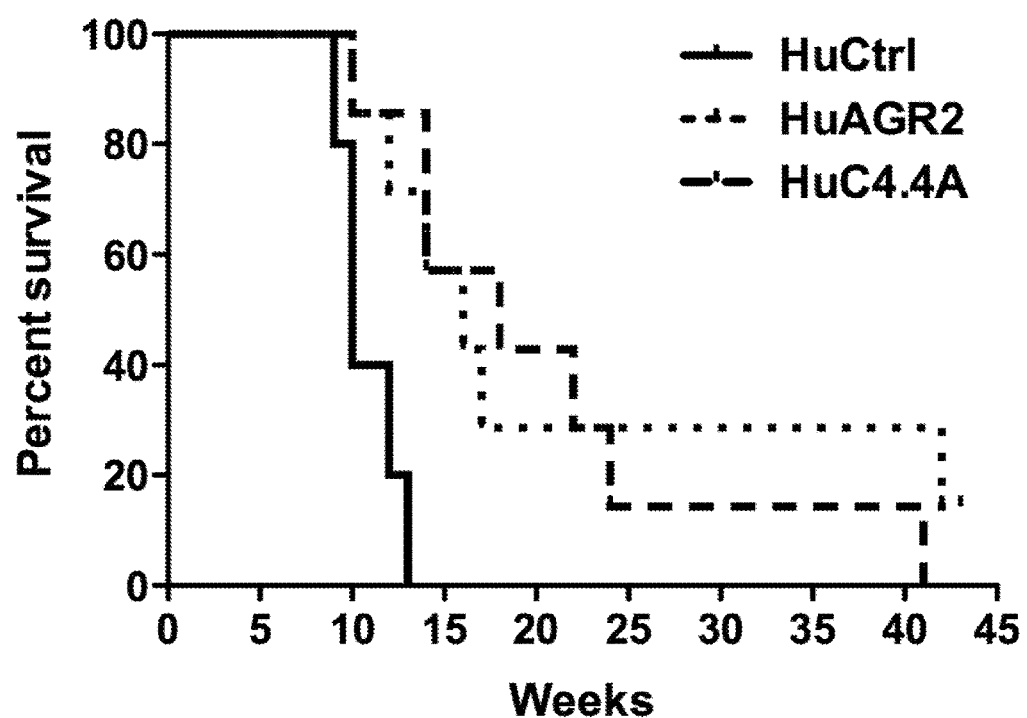
FIG. 12. Survival Curve in Capan-2 Tumors. Graph shows a survival curve of mice with Capan-2 tumors formed orthotopically and treated with control human IgG (HuCtr1), humanized anti-AGR2 mAb (HuAGR2) or humanized anti-C4.4A mAb (HuC4.4A) antibodies.

Orthotopic tumors were developed with CaPan-2 cells (1.50 million cells) labelled with luciferase and allowed the tumor to grow bigger until it reached approximately 1 g size of tumor (5 weeks) as measured in parallel experiments. Mice were treated with either Vehicle (human IgG Isotype control—Cat #0160-01, Southern Biotech, Birmingham, Ala.) indicated as HuCtrl, n=5, or AGR2 humanized Ab, indicated as HuAGR2, n=7, or C4.4A humanized Ab indicated as HuC4.4A, n=7, (25 mg/kg b.wt/i.p./twice a week) until 40 weeks. Tumor was measured every week by bioluminescence imaging. Survival curve was measured as shown in FIG. 12. At the time when control group showed 100% death, HuAGR2 group showed 71% survival and HuC4.4A showed 87% survival. Median survival was 10 weeks for control, 16 weeks for HuAGR2 and 18 weeks for HuC4.4A groups. Comparison of survival curves (Log-Rank Mantel Cox test) suggested that HuAGR2 (p=0.0118) and HuC4.4A (p=0.0032) treated groups showed significant improvement in survival as compared to control group. (p<0.05)

Prophetic Example 9

Determination of the Binding Epitopes for 163-28B-1 and 162-1A-1 Antibodies

Binding epitopes for the 163-28B-1 and 162-1A-1 can be experimentally determined. Systematic mutations in AGR2 and C4.4A protein sequences can be introduced, and the antibody binding of the resulting sequences can be measured to identify amino acids that comprise an epitope. This technique can be used to map both linear and conformational epitopes. High throughput mutagenesis mapping is another approach which utilizes a comprehensive mutation library, with each clone containing a unique amino acid mutation (conservative, non-conservative, or alanine) and the entire library covering every amino acid in the target protein. Hundreds of plasmid clones from the mutation library are individually arrayed in 384-well micro plates, expressed in mammalian cells and tested for antibody binding. Amino acids that are required for antibody binding can be identified by a loss of fluorescent reactivity and mapped onto protein structures to visualize epitopes.

\* \* \*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,469,797
U.S. Pat. No. 4,472,509
U.S. Pat. No. 4,606,855
U.S. Pat. No. 4,703,003
U.S. Pat. No. 4,742,159
U.S. Pat. No. 4,767,720
U.S. Pat. No. 4,816,567
U.S. Pat. No. 4,867,973
U.S. Pat. No. 4,870,287
U.S. Pat. No. 4,938,948
U.S. Pat. No. 4,946,778

U.S. Pat. No. 5,021,236
U.S. Pat. No. 5,091,513
U.S. Pat. No. 5,164,296
U.S. Pat. No. 5,196,066
U.S. Pat. No. 5,223,409
U.S. Pat. No. 5,403,484
U.S. Pat. No. 5,420,253
U.S. Pat. No. 5,565,332
U.S. Pat. No. 5,571,698
U.S. Pat. No. 5,627,052
U.S. Pat. No. 5,656,434
U.S. Pat. No. 5,739,169
U.S. Pat. No. 5,760,395
U.S. Pat. No. 5,770,376
U.S. Pat. No. 5,789,208
U.S. Pat. No. 5,801,005
U.S. Pat. No. 5,821,337
U.S. Pat. No. 5,824,311
U.S. Pat. No. 5,830,880
U.S. Pat. No. 5,844,091
U.S. Pat. No. 5,846,945
U.S. Pat. No. 5,858,657
U.S. Pat. No. 5,861,155
U.S. Pat. No. 5,871,907
U.S. Pat. No. 5,969,108
U.S. Pat. No. 6,054,297
U.S. Pat. No. 6,165,464
U.S. Pat. No. 6,365,157
U.S. Pat. No. 6,406,867
U.S. Pat. No. 6,709,659
U.S. Pat. No. 6,709,873
U.S. Pat. No. 6,753,407
U.S. Pat. No. 6,814,965
U.S. Pat. No. 6,849,259
U.S. Pat. No. 6,861,572
U.S. Pat. No. 6,875,434
U.S. Pat. No. 6,881,557
U.S. Pat. No. 6,891,024
U.S. Pat. No. 6,946,546
U.S. Pat. No. 7,407,659
U.S. Pat. No. 8,178,098

Aberger et al., Anterior specification of embryonic ectoderm: the role of the *Xenopus* cement gland-specific gene XAG-2. *Mech. Dev.*, 72:115-130, 1998.

Altschul et al., Gapped BLAST and PSI-BLAST: a new generation of protein database search programs. *Nucleic Acids Res.*, 25:3389-3402, 1997.

Arumugam et al., Epithelial to mesenchymal transition contributes to drug resistance in pancreatic cancer. *Cancer Res.*, 69:5820-5828, 2009.

Austin-Ward and Villaseca, *Revista Medica de Chile*, 126(7):838-845, 1998.

Barbas et al., *Proc. Natl. Acad. Sci., USA*, 91:3809-3813, 1994.

Barraclough et al., The metastasis-associated anterior gradient 2 protein is correlated with poor survival of breast cancer patients. *Am. J. Pathol.*, 175:1848-1857, 2009.

Brychtova et al., Anterior gradient 2: a novel player in tumor cell biology. *Cancer Lett.*, 304:1-7, 2011.

Bukowski et al., *Clinical Cancer Res.*, 4(10):2337-2347, 1998.

Chatterjee and Mayor, The GPI-anchor and protein sorting. *Cell. Mol. Life Sci.*, 58:1969-1987, 2001.

Christodoulides et al., *Microbiology*, 144(Pt 11):3027-3037, 1998.

da Silva et al., The newt ortholog of CD59 is implicated in proximodistal identity during amphibian limb regeneration. *Dev. Cell.*, 3:547-555, 2002.

Davidson et al., *J. Immunother.*, 21(5):389-398, 1998.

Dumartin et al., AGR2 is a novel surface antigen that promotes the dissemination of pancreatic cancer cells through regulation of cathepsins B and D. *Cancer Res.*, 71:7091-7102, 2011.

Fletcher et al., hAG-2 and hAG-3, human homologues of genes involved in differentiation, are associated with oestrogen receptor-positive breast tumours and interact with metastasis gene C4.4a and dystroglycan. *Br. J. Cancer*, 88:579-585, 2003.

Galat, The three-fingered protein domain of the human genome. *Cell. Mol. Life Sci.*, 65:3481-3493, 2008.

Goldfinger et al., The alpha3 laminin subunit, alpha6beta4 and alpha3beta1 integrin coordinately regulate wound healing in cultured epithelial cells and in the skin. *J. Cell Sci.*, 112:2615-2629, 1999.

Gram et al., *Proc. Natl. Acad. Sci. USA*, 89:3576-3580, 1992.

Gupta et al., AGR2 gene function requires a unique endoplasmic reticulum localization motif. *J. Biol. Chem.*, 287:4773-4782, 2012.

Hanibuchi et al., *Int. J. Cancer*, 78(4):480-485, 1998.

Hansen et al., Tumour cell expression of C4.4A, a structural homologue of the urokinase receptor, correlates with poor prognosis in non-small cell lung cancer. *Lung Cancer*, 58:260-266, 2007.

Hellstrand et al., *Acta Oncologica*, 37(4):347-353, 1998.

Higa et al., Role of the pro-oncogenic Protein Disulfide Isomerase (PDI)-family member Anterior Gradient 2 (AGR2) in the control of endoplasmic reticulum homeostasis. *J. Biol. Chem.*, 286:44855-44868, 2011.

Hollander, *Front. Immun.*, 3:3, 2012.

Hu et al., *Cancer Res.*, 56:3055-3061, 1996.

Hui and Hashimoto, *Infection Immun.*, 66(11):5329-5336, 1998.

Innes et al., Significance of the metastasis-inducing protein AGR2 for outcome in hormonally treated breast cancer patients. *Br. J. Cancer*, 94:1057-1065, 2006.

Jacobsen and Ploug, The urokinase receptor and its structural homologue C4.4A in human cancer: expression, prognosis and pharmacological inhibition. *Curr. Med. Chem.*, 5:2559-2573, 2008.

Jiang et al., Distinct distribution of laminin and its integrin receptors in the pancreas. *J. Histochem. Cytochem.*, 50:1625-1632, 2002.

Kabat et al., Sequences of Proteins of Immunological Interests, Fifth edition, NIH Publication No. 91-3242, U.S. Department of Health and Human Services, 1991.

Komiya et al., Cloning of the gene gob-4, which is expressed in intestinal goblet cells in mice. *Biochim. Biophys. Acta.*, 1444:434-438, 1999.

Konishi et al., Expression of C4.4A at the invasive front is a novel prognostic marker for disease recurrence of colorectal cancer. *Cancer Sci.*, 101:2269-2277, 2010.

Kumar et al., Positional identity of adult stem cells in salamander limb regeneration. *C. R. Biol.*, 330:485-490, 2007.

Liu et al., *Cell Mol. Biol.*, 49:209-216, 2003.

Liu et al., Human homologue of cement gland protein, a novel metastasis inducer associated with breast carcinomas. *Cancer Res.*, 65:3796-3805, 2005.

Logsdon et al., Molecular profiling of pancreatic adenocarcinoma and chronic pancreatitis identifies multiple genes differentially regulated in pancreatic cancer. *Cancer Res.*, 63:2649-2657, 2003.

Marks et al., *Bio/Technol.*, 10:779-783, 1992.

Ngora et al., Membrane-Bound and Exosomal Metastasis-Associated C4.4A Promotes Migration by Associating with the α(6)β(4) Integrin and MT1-MMP. *Neoplasia*, 14:95-107, 2012.

Norris et al., AGR2 is a SMAD4-suppressible gene that modulates MUC1 levels and promotes the initiation and progression of pancreatic intraepithelial neoplasia. *Oncogene*, 32:3867-3876, 2013.

Paret et al., Ly6 family member C4.4A binds laminins 1 and 5, associates with galectin-3 and supports cell migration. *Int. J. Cancer*, 115:724-733, 2005.

Paret et al., C4.4A as a candidate marker in the diagnosis of colorectal cancer. *Br. J. Cancer*, 97:1146-1156, 2007.

Park et al., The protein disulfide isomerase AGR2 is essential for production of intestinal mucus. *Proc. Natl. Acad. Sci. USA*, 106:6950-6955, 2009.

Persson et al., Diversity of the protein disulfide isomerase family: identification of breast tumor induced Hag2 and Hag3 as novel members of the protein family. *Mol. Phylogenet. Evol.*, 36:734-740, 2005.

Qin et al., *Proc. Natl. Acad. Sci. USA*, 95(24):14411-14416, 1998.

Ramachandran et al., Adrenomedullin is expressed in pancreatic cancer and stimulates cell proliferation and invasion in an autocrine manner via the adrenomedullin receptor, ADMR. *Cancer Res.*, 67:2666-2675, 2007.

Ramachandran et al., Anterior gradient 2 is expressed and secreted during the development of pancreatic cancer and promotes cancer cell survival. *Cancer Res.*, 68:7811-7818, 2008.

Rösel et al., Cloning and functional characterization of a new phosphatidyl-inositol anchored molecule of a metastasizing rat pancreatic tumor. *Oncogene*, 17:1989-2002, 1998.

Schier et al., *Gene*, 169(2):147-155, 1996.

Seiter et al., Upregulation of C4.4A expression during progression of melanoma. *J. Invest. Dermatol.*, 116:344-347, 2001.

Smirnov et al., Global gene expression profiling of circulating tumor cells. *Cancer Res.*, 65:4993-4997, 2005.

Smith et al., Identification of genes involved in human urothelial cell-matrix interactions: implications for the progression pathways of malignant urothelium. *Cancer Res.*, 61:1678-1685, 2001.

Smith and Marshall, Regulation of cell signalling by uPAR. *Nat. Rev. Mol. Cell. Biol.*, 11:23-36, 2010.

Stemmer, *Nature*, 370:389-391, 1994.

Symington and Carter. Modulation of epidermal differentiation by epiligrin and integrin alpha 3 beta 1. *J. Cell Sci.*, 108:831-838, 1995.

Thompson and Weigel, hAG-2, the human homologue of the *Xenopus laevis* cement gland gene XAG-2, is coexpressed with estrogen receptor in breast cancer cell lines. *Biochem Biophys. Res. Commun.*, 251:111-116, 1998.

Wang et al., The adenocarcinoma-associated antigen, AGR2, promotes tumor growth, cell migration, and cellular transformation. *Cancer Res.*, 68:492-497, 2008.

Würfel et al., Cloning of the human homologue of the metastasis-associated rat C4.4A. *Gene*, 262:35-41, 2001.

Xue et al., Suppression of urokinase plasminogen activator receptor inhibits proliferation and migration of pancreatic adenocarcinoma cells via regulation of ERK/p38 signaling. *Int. J. Biochem. Cell. Biol.*, 41:1731-1738, 2009.

Zhang et al., AGR2, an androgen-inducible secretory protein overexpressed in prostate cancer. *Genes Chromosomes Cancer*, 43:249-259, 2005.

Zhao et al., Disruption of Paneth and goblet cell homeostasis and increased endoplasmic reticulum stress in Agr2-/- mice. *Dev. Biol.*, 338:270-279, 2010.

Zhu et al., High resolution analysis of genomic aberrations by metaphase and array comparative genomic hybridization identifies candidate tumour genes in lung cancer cell lines. *Cancer Lett.*, 245:303-314, 2007.

What is claimed is:

1. An isolated monoclonal antibody or antigen binding fragment thereof which binds to an AGR2 polypeptide and comprises:
   (a) a first $V_H$ CDR which is identical to SEQ ID NO: 20;
   (b) a second $V_H$ CDR which is identical to SEQ ID NO: 21;
   (c) a third $V_H$ CDR which is identical to SEQ ID NO: 22;
   (d) a first $V_L$ CDR which is identical to SEQ ID NO: 23;
   (e) a second $V_L$ CDR which is identical to SEQ ID NO: 24; and
   (f) a third $V_L$ CDR which is identical to SEQ ID NO: 25.

2. The isolated monoclonal antibody or antigen binding fragment of claim 1, which comprises:
   (a) a first $V_H$ CDR which is identical to SEQ ID NO: 20;
   (b) a second $V_H$ CDR which is identical to SEQ ID NO: 21;
   (c) a third $V_H$ CDR which is identical to SEQ ID NO: 22; and
   (d) a $V_L$ domain which is identical to SEQ ID NO: 19.

3. The isolated monoclonal antibody or antigen binding fragment thereof of claim 1, which comprises:
   (a) a $V_H$ domain identical to SEQ ID NO: 18;
   (b) a first $V_L$ CDR which is identical to SEQ ID NO: 23;
   (c) a second $V_L$ CDR which is identical to SEQ ID NO: 24; and
   (d) a third $V_L$ CDR which is identical to SEQ ID NO: 25.

4. The isolated monoclonal antibody or antigen binding fragment thereof of claim 1, which comprises a $V_H$ domain identical to the $V_H$ domain of 163-28B-1 (SEQ ID NO: 18) and a $V_L$ domain identical to the $V_L$ domain of 163-28B-1 (SEQ ID NO: 19).

5. The isolated monoclonal antibody or an antigen binding fragment thereof of claim 1, wherein the isolated monoclonal antibody or an antigen binding fragment thereof inhibits the migration of pancreatic ductal adenocarcinoma tumor cells and resistance of the tumor cells to gemcitabine-induced apoptosis.

6. The isolated monoclonal antibody or antigen binding fragment thereof of claim 1, wherein the isolated monoclonal antibody is a recombinant.

7. The isolated monoclonal antibody or antigen binding fragment thereof of claim 1, wherein the isolated monoclonal antibody or antigen binding fragment thereof is an IgG, IgM, IgA isotype.

8. The isolated monoclonal antibody or antigen binding fragment thereof of claim 1, wherein the isolated monoclonal antibody or antigen binding fragment thereof is a Fab', a F(ab')2, a F(ab')3, a monovalent scFv, or a bivalent scFv.

9. The isolated monoclonal antibody or antigen binding fragment thereof of claim 1, wherein the isolated monoclonal antibody or antigen binding fragment thereof is a humanized antibody or de-immunized antibody.

10. The isolated monoclonal antibody or antigen binding fragment thereof of claim 1, wherein the isolated monoclonal antibody or antigen binding fragment thereof is conjugated to an imaging agent, a chemotherapeutic agent, a toxin, or a radionucleotide.

11. A composition comprising an isolated monoclonal antibody or antigen binding fragment thereof of claim 1, and a pharmaceutically acceptable carrier or diluent.

12. A method for treating a human subject having pancreatic cancer comprising administering an effective amount of an isolated monoclonal antibody or antigen binding fragment thereof of claim 1 to the subject.

13. The method of claim 12, wherein the pancreatic cancer is pancreatic ductal adenocarcinoma.

14. The method of claim 12, wherein the isolated monoclonal antibody or antigen binding fragment thereof is administered systemically.

15. The method of claim 12, wherein the isolated monoclonal antibody or antigen binding fragment thereof is administered intravenously, intradermally, intratumorally, intramuscularly, intraperitoneally, subcutaneously, or locally.

16. The method of claim 12, further comprising administering at least a second anti-cancer therapy to the subject.

17. The method of claim 16, wherein the second anti-cancer therapy is a surgical therapy, chemotherapy, radiation therapy, cryotherapy, hormonal therapy, immunotherapy or cytokine therapy.

* * * * *

SEQUENCE LISTING

```
<160> NUMBER OF SEQ ID NOS: 29

<210> SEQ ID NO 1
<211> LENGTH: 528
<212> TYPE: RNA
<213> ORGANISM: Homo sapiens

<400> SEQUENCE: 1
auggagaaaa uuccaguguc agcauucuug cuccuugugg cccucuccua cacucuggcc      60
agagauacca cagucaaacc uggagccaaa aaggacacaa aggacucucg acccaaacug     120
ccccagaccc ucuccagagg uuggggugac caacucaucu ggacucagac auaugaagaa     180
gcucuauaua aauccaagac aagcaacaaa cccuugauga uuauucauca cuuggaugag     240
ugcccacaca gucaagcuuu aaagaaagug uuugcugaaa auaaagaaau ccagaaauug     300
gcagagcagu uugucuccu caaucugguu uaugaaacaa cugacaaaca ccuuucuccu     360
gauggccagu augucccag gauuauguuu guugacccau cucugacagu uagagccgau     420
aucacuggaa gauauucaaa ucgucucuau gcuuacgaac cugcagauac agcucuguug     480
cuugacaaca ugaagaaagc ucucaaguug cugaagacug aauuguaa                  528
```

<210> SEQ ID NO 2
<211> LENGTH: 1041
<212> TYPE: RNA
<213> ORGANISM: Homo sapiens

<400> SEQUENCE: 2

```
auggaccccg ccaggaaagc aggugcccag gccaugaucu ggacugcagg cuggcugcug      60
cugcugcugc uucgcggagg agcgcaggcc cuggagugcu acagcugcgu gcagaaagca     120
gaugacggau gcuccccgaa caagaugaag acagugaagu gcgcgccggg cguggacguc     180
ugcaccgagg ccguggggc ggugagacc auccacggac aauucucgcu ggcagugcgg      240
gguugcgguu cgggacuccc cggcaagaau gaccgcggcc uggaucuuca cgggcuucg      300
gcguucaucc agcugcagca augcgcucag gaucgcugca acgccaagcu caaccucacc     360
ucgcgggcgc ucgaccccgc agguaaugag agugcauacc cgcccaacgg cguggagugc     420
uacagcugug ugggccugag ccgggaggcg ugccagggua caucgccgcc ggucgugagc     480
ugcuacaacg ccagcgauca ugucuacaag ggcugcuucg acggcaacgu caccuugacg     540
gcagcuaaug ugacugugc cuugccuguc cggggcugug uccaggauga auucugcacu      600
cgggauggag uaacaggccc agguucacg cucagugggcu ccuguugcca ggguccccgc    660
uguaacucug accuccgcaa caagaccuac uucuccccuc gaaucccacc ccuuguccgg     720
cugcccccuc cagagcccac gacuguggcc ucaaccacau cugucaccac uucuaccucg     780
gccccaguga cccacaauc caccaccaaa cccaugccag cgccaaccag ucagacuccg     840
agacagggag uagaacacga ggccuccegg gaugaggagc ccaggugac uggaggcgcc     900
gcuggccacc aggaccgcag caauucaggg caguauccug caaaaggggg gccccagcag     960
ccccauaaua aaggcugugu ggcucccaca gcuggauugg cagcccuucu guuggccgug    1020
gcugcugguu ucccuacugug a                                             1041
```

<210> SEQ ID NO 3
<211> LENGTH: 30
<212> TYPE: PRT
<213> ORGANISM: Artificial Sequence
<220> FEATURE:
<223> OTHER INFORMATION: Synthetic peptide

<400> SEQUENCE: 3

Cys Ile His His Leu Asp Glu Ser Pro His Ser Gln Ala Leu Lys Lys
1               5                   10                  15
Val Phe Ala Glu Asn Lys Glu Ile Gln Lys Leu Ala Glu Gln
            20                  25                  30

<210> SEQ ID NO 4
<211> LENGTH: 36
<212> TYPE: PRT
<213> ORGANISM: Artificial Sequence
<220> FEATURE:
<223> OTHER INFORMATION: Synthetic peptide

<400> SEQUENCE: 4

Cys Pro Val Arg Pro Thr Ser Thr Thr Lys Pro Met Pro Ala Pro Thr
1               5                   10                  15
Ser Gln Thr Pro Arg Gln Gly Val Glu His Glu Ala Ser Arg Asp Glu
            20                  25                  30
Glu Pro Arg Leu
        35

-continued

```
<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gccagtggat agacagatgg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
gccagtggat agactgatgg                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
gatggataca gttggtgcag c                                             21

<210> SEQ ID NO 8
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 8
cgactcacta tagggagagc ggc                                           23

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
aagaacatcg attttccatg gcag                                          24

<210> SEQ ID NO 10
<211> LENGTH: 139
<212> TYPE: PRT
<213> ORGANISM: Artificial Sequence
<220> FEATURE:
<223> OTHER INFORMATION: Synthetic peptide

<400> SEQUENCE: 10

Met Asn Phe Gly Leu Ser Leu Ile Phe Leu Val Leu Ile Leu Lys Gly
 1               5                  10                  15

Val Gln Cys Glu Val Met Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
```

```
            50                  55                  60
Glu Trp Val Ala Ser Ile Ser Ser Gly Gly Gly Asn Thr Tyr Tyr Ala
 65                  70                  75                  80

Asp Ser Val Lys Gly Arg Phe Thr Met Ser Arg Asp Asn Ala Lys Asn
                 85                  90                  95

Asn Leu Tyr Leu Gln Met Ser Ser Leu Arg Ser Glu Asp Thr Ala Leu
                100                 105                 110

Tyr Tyr Cys Ala Arg Ser Tyr Tyr Gly Ile Ser Tyr Asp Thr Tyr
            115                 120                 125

Trp Gly Gln Gly Thr Leu Val Thr Val Ser Ala
            130                 135

<210> SEQ ID NO 11
<211> LENGTH: 131
<212> TYPE: PRT
<213> ORGANISM: Artificial Sequence
<220> FEATURE:
<223> OTHER INFORMATION: Synthetic peptide

<400> SEQUENCE: 11

Met Lys Leu Pro Val Arg Leu Leu Val Leu Met Phe Trp Ile Pro Ala
  1               5                  10                  15

Ser Asn Ser Asp Val Val Met Thr Gln Thr Pro Leu Ser Leu Pro Val
                 20                  25                  30

Ser Leu Gly Asp Gln Ala Ser Ile Ser Cys Arg Ser Ser Gln Asn Leu
             35                  40                  45

Val His Ser Asp Gly Asn Thr Tyr Leu His Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
                100                 105                 110

Ser Gln Ser Thr His Val Pro Tyr Thr Phe Gly Gly Gly Thr Lys Leu
            115                 120                 125

Glu Ile Lys
    130

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Ser Tyr Thr Met Ser
  1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide

<400> SEQUENCE: 13

Ser Ile Ser Ser Gly Gly Gly Asn Thr Tyr Tyr Ala Asp Ser Val Lys
  1               5                  10                  15
```

Gly

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Ser Tyr Tyr Tyr Gly Ile Ser Tyr Asp Thr Tyr
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Arg Ser Ser Gln Asn Leu Val His Ser Asp Gly Asn Thr Tyr Leu His
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Lys Val Ser Asn Arg Phe Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Ser Gln Ser Thr His Val Pro Tyr Thr
1               5

<210> SEQ ID NO 18
<211> LENGTH: 136
<212> TYPE: PRT
<213> ORGANISM: Artificial Sequence
<220> FEATURE:
<223> OTHER INFORMATION: Synthetic peptide

<400> SEQUENCE: 18

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asp Thr Gly Lys Pro Thr Tyr Thr
65                  70                  75                  80

Glu Glu Phe Lys Gly Arg Phe Ala Phe Ser Leu Ala Thr Ser Ala Ser
                85                  90                  95

Thr Ala Tyr Leu Gln Ile Asn Asn Leu Arg Asn Glu Asp Thr Ala Thr
            100                 105                 110

Tyr Phe Cys Gly Arg Val Thr Ala Asp Ser Met Asp Tyr Trp Gly Gln
        115                 120                 125

Gly Thr Ser Val Thr Val Ser Ser
    130                 135

<210> SEQ ID NO 19
<211> LENGTH: 131
<212> TYPE: PRT
<213> ORGANISM: Artificial Sequence
<220> FEATURE:
<223> OTHER INFORMATION: Synthetic peptide

<400> SEQUENCE: 19

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Ile Tyr Leu His Trp Phe Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Lys Leu
        115                 120                 125

Glu Leu Lys
    130

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Asn Tyr Gly Met Asn
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide

<400> SEQUENCE: 21

Trp Ile Asn Thr Asp Thr Gly Lys Pro Thr Tyr Thr Glu Glu Phe Lys
1               5                   10                  15

Gly

-continued

```
<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Val Thr Ala Asp Ser Met Asp Tyr
1               5

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide

<400> SEQUENCE: 23

Arg Ser Ser Gln Ser Leu Val His Ser Asn Gly Asn Ile Tyr Leu His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Lys Val Ser Asn Arg Phe Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Ser Gln Ser Thr His Val Pro Leu Thr
1               5

<210> SEQ ID NO 26
<211> LENGTH: 175
<212> TYPE: PRT
<213> ORGANISM: Homo sapiens

<400> SEQUENCE: 26

Met Glu Lys Ile Pro Val Ser Ala Phe Leu Leu Leu Val Ala Leu Ser
1               5                   10                  15

Tyr Thr Leu Ala Arg Asp Thr Thr Val Lys Pro Gly Ala Lys Lys Asp
                20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
65                  70                  75                  80

Cys Pro His Ser Gln Ala Leu Lys Lys Val Phe Ala Glu Asn Lys Glu
                85                  90                  95

Ile Gln Lys Leu Ala Glu Gln Phe Val Leu Leu Asn Leu Val Tyr Glu
                100                 105                 110
```

```
Thr Thr Asp Lys His Leu Ser Pro Asp Gly Gln Tyr Val Pro Arg Ile
            115                 120                 125

Met Phe Val Asp Pro Ser Leu Thr Val Arg Ala Asp Ile Thr Gly Arg
130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175

<210> SEQ ID NO 27
<211> LENGTH: 346
<212> TYPE: PRT
<213> ORGANISM: Homo sapiens

<400> SEQUENCE: 27

Met Asp Pro Ala Arg Lys Ala Gly Ala Gln Ala Met Ile Trp Thr Ala
1               5                   10                  15

Gly Trp Leu Leu Leu Leu Leu Arg Gly Gly Ala Gln Ala Leu Glu
            20                  25                  30

Cys Tyr Ser Cys Val Gln Lys Ala Asp Asp Gly Cys Ser Pro Asn Lys
        35                  40                  45

Met Lys Thr Val Lys Cys Ala Pro Gly Val Asp Val Cys Thr Glu Ala
    50                  55                  60

Val Gly Ala Val Glu Thr Ile His Gly Gln Phe Ser Leu Ala Val Arg
65                  70                  75                  80

Gly Cys Gly Ser Gly Leu Pro Gly Lys Asn Asp Arg Gly Leu Asp Leu
                85                  90                  95

His Gly Leu Leu Ala Phe Ile Gln Leu Gln Gln Cys Ala Gln Asp Arg
            100                 105                 110

Cys Asn Ala Lys Leu Asn Leu Thr Ser Arg Ala Leu Asp Pro Ala Gly
        115                 120                 125

Asn Glu Ser Ala Tyr Pro Pro Asn Gly Val Glu Cys Tyr Ser Cys Val
    130                 135                 140

Gly Leu Ser Arg Glu Ala Cys Gln Gly Thr Ser Pro Pro Val Val Ser
145                 150                 155                 160

Cys Tyr Asn Ala Ser Asp His Val Tyr Lys Gly Cys Phe Asp Gly Asn
                165                 170                 175

Val Thr Leu Thr Ala Ala Asn Val Thr Val Ser Leu Pro Val Arg Gly
            180                 185                 190

Cys Val Gln Asp Glu Phe Cys Thr Arg Asp Gly Val Thr Gly Pro Gly
        195                 200                 205

Phe Thr Leu Ser Gly Ser Cys Cys Gln Gly Ser Arg Cys Asn Ser Asp
    210                 215                 220

Leu Arg Asn Lys Thr Tyr Phe Ser Pro Arg Ile Pro Pro Leu Val Arg
225                 230                 235                 240

Leu Pro Pro Pro Glu Pro Thr Thr Val Ala Ser Thr Thr Ser Val Thr
                245                 250                 255

Thr Ser Thr Ser Ala Pro Val Arg Pro Thr Ser Thr Thr Lys Pro Met
            260                 265                 270

Pro Ala Pro Thr Ser Gln Thr Pro Arg Gln Gly Val Glu His Glu Ala
        275                 280                 285

Ser Arg Asp Glu Glu Pro Arg Leu Thr Gly Gly Ala Ala Gly His Gln
    290                 295                 300

Asp Arg Ser Asn Ser Gly Gln Tyr Pro Ala Lys Gly Gly Pro Gln Gln
```

```
305                 310                 315                 320
Pro His Asn Lys Gly Cys Val Ala Pro Thr Ala Gly Leu Ala Ala Leu
                325                 330                 335

Leu Leu Ala Val Ala Ala Gly Val Leu Leu
            340                 345

<210> SEQ ID NO 28
<211> LENGTH: 29
<212> TYPE: PRT
<213> ORGANISM: Homo sapiens

<400> SEQUENCE: 28

Ile His His Leu Asp Glu Cys Pro His Ser Gln Ala Leu Lys Lys Val
1               5                   10                  15

Phe Ala Glu Asn Lys Glu Ile Gln Lys Leu Ala Glu Gln
            20                  25

<210> SEQ ID NO 29
<211> LENGTH: 35
<212> TYPE: PRT
<213> ORGANISM: Homo sapiens

<400> SEQUENCE: 29

Pro Val Arg Pro Thr Ser Thr Thr Lys Pro Met Pro Ala Pro Thr Ser
1               5                   10                  15

Gln Thr Pro Arg Gln Gly Val Glu His Glu Ala Ser Arg Asp Glu Glu
            20                  25                  30

Pro Arg Leu
        35
```